US010980273B2

(12) United States Patent
Verleur et al.

(10) Patent No.: US 10,980,273 B2
(45) Date of Patent: Apr. 20, 2021

(54) VAPORIZER, CHARGER AND METHODS OF USE

(71) Applicant: VMR Products, LLC, Miami, FL (US)

(72) Inventors: Jan Andries Verleur, Miami Beach, FL (US); Dan Recio, Miami, FL (US); Yifeng Lu, Miami, FL (US); Yinjun Zhang, Miami, FL (US); Arturo Fajardo, Miami, FL (US); Hans Verleur, El Dorado, CA (US)

(73) Assignee: VMR Products, LLC, San Francisco, CA (US)

( * ) Notice: Subject to any disclaimer, the term of this patent is extended or adjusted under 35 U.S.C. 154(b) by 192 days.

(21) Appl. No.: 14/201,267

(22) Filed: Mar. 7, 2014

(65) Prior Publication Data

US 2015/0128972 A1    May 14, 2015

Related U.S. Application Data

(63) Continuation of application No. 14/196,729, filed on Mar. 4, 2014, now Pat. No. 10,039,321.

(Continued)

(51) Int. Cl.

| | |
|---|---|
| *A24F 47/00* | (2020.01) |
| *A24F 40/00* | (2020.01) |
| *A61M 11/04* | (2006.01) |
| *A61M 15/06* | (2006.01) |
| *H02J 7/00* | (2006.01) |
| *A24F 40/40* | (2020.01) |

(52) U.S. Cl.
CPC .......... *A24F 40/00* (2020.01); *A61M 11/042* (2014.02); *A61M 15/06* (2013.01); *H02J 7/00* (2013.01); *H02J 7/0042* (2013.01); *A24F 40/40* (2020.01); *A61M 2205/332* (2013.01); *A61M 2205/3368* (2013.01); *A61M 2205/502* (2013.01); *A61M 2205/584* (2013.01); *A61M 2205/8206* (2013.01); *A61M 2205/8237* (2013.01)

(58) Field of Classification Search
CPC ................... A24F 47/008; H02J 7/0042–0044
USPC ............................... 320/107–115; 439/38–40
See application file for complete search history.

(56) References Cited

U.S. PATENT DOCUMENTS

| | | | |
|---|---|---|---|
| 1,446,087 A | 2/1923 | Griffin | |
| 2,057,353 A | 10/1936 | Whittemore, Jr. | |

(Continued)

FOREIGN PATENT DOCUMENTS

| | | |
|---|---|---|
| AU | 201406215 A1 | 8/2014 |
| AU | 2014206215 A1 | 8/2014 |

(Continued)

OTHER PUBLICATIONS

European Patent Office Search Report dated Oct. 12, 2015 for EP Application No. 14159710.4, filed Mar. 14, 2014.

(Continued)

*Primary Examiner* — Eric Yaary
(74) *Attorney, Agent, or Firm* — Mintz Levin Cohn Ferris Glovsky and Popeo, P.C.

(57) ABSTRACT

Vaporizer and/or electronic cigarette chargers useful for the recharging of rechargeable vaporizer or electronic cigarette power supplies such as batteries, compatible vaporizers and/or electronic cigarettes, their components, charging contacts, methods of their use and kits containing such chargers are disclosed.

22 Claims, 18 Drawing Sheets

Related U.S. Application Data

(60) Provisional application No. 61/937,951, filed on Feb. 10, 2014, provisional application No. 61/903,344, filed on Nov. 12, 2013.

(56) References Cited

U.S. PATENT DOCUMENTS

| | | |
|---|---|---|
| 2,545,851 A | 3/1951 | Kardos |
| 3,060,429 A | 10/1962 | Winston |
| 3,085,145 A | 4/1963 | Wray |
| 3,200,819 A | 8/1965 | Gilbert |
| 3,203,025 A | 8/1965 | Schreur |
| 3,258,015 A | 6/1966 | Drummond et al. |
| 3,400,998 A | 9/1968 | Daugherty et al. |
| 3,479,561 A | 11/1969 | Janning |
| 3,502,588 A | 3/1970 | Winberg |
| 3,521,216 A | 7/1970 | Tolegian |
| 3,747,120 A | 7/1973 | Stemme |
| 3,918,451 A | 11/1975 | Steil |
| 3,934,117 A | 1/1976 | Schladitz |
| D248,047 S | 5/1978 | Rappoport |
| D251,072 S | 2/1979 | Stuetzer |
| 4,171,000 A | 10/1979 | Uhle |
| 4,207,457 A | 6/1980 | Haglund et al. |
| D257,519 S | 11/1980 | Plozner |
| D259,588 S | 6/1981 | Stutzer |
| D260,690 S | 9/1981 | Stutzer |
| D260,941 S | 9/1981 | Figur |
| 4,569,136 A | 2/1986 | Loring |
| 4,676,237 A | 6/1987 | Wood et al. |
| 4,745,705 A | 5/1988 | Yamamoto et al. |
| 4,771,295 A | 9/1988 | Baker et al. |
| 4,771,796 A | 9/1988 | Myer |
| 4,793,365 A | 12/1988 | Sensabaugh et al. |
| 4,797,692 A | 1/1989 | Ims |
| 4,811,731 A | 3/1989 | Newell et al. |
| 4,848,374 A | 7/1989 | Chard et al. |
| 4,941,236 A | 7/1990 | Sherman et al. |
| 4,945,448 A | 8/1990 | Bremenour et al. |
| 4,945,929 A | 8/1990 | Egilmex |
| 4,947,874 A | 8/1990 | Brooks et al. |
| 4,947,875 A | 8/1990 | Brooks et al. |
| 4,972,855 A | 11/1990 | Kuriyama et al. |
| 4,990,939 A | 2/1991 | Sekiya et al. |
| 4,993,436 A | 2/1991 | Bloom |
| 5,020,548 A | 6/1991 | Farrier et al. |
| 5,042,509 A | 8/1991 | Banerjee et al. |
| 5,050,621 A | 9/1991 | Creighton et al. |
| 5,060,671 A | 10/1991 | Counts et al. |
| 5,117,482 A | 5/1992 | Hauber |
| 5,124,200 A | 6/1992 | Mallonee |
| 5,144,962 A | 9/1992 | Counts et al. |
| 5,224,265 A | 7/1993 | Dux et al. |
| 5,224,498 A | 7/1993 | Deevi et al. |
| 5,249,586 A | 10/1993 | Morgan et al. |
| 5,261,424 A | 11/1993 | Sprinkel |
| 5,269,327 A | 12/1993 | Counts et al. |
| 5,327,915 A | 7/1994 | Porenski et al. |
| 5,345,951 A | 9/1994 | Serrano et al. |
| 5,372,148 A | 12/1994 | Mccafferty et al. |
| 5,388,574 A | 2/1995 | Ingebrethsen |
| 5,479,948 A | 1/1996 | Counts et al. |
| 5,505,214 A | 4/1996 | Collins et al. |
| 5,646,666 A | 7/1997 | Cowger et al. |
| 5,666,977 A | 9/1997 | Higgins et al. |
| 5,682,050 A | 10/1997 | Williams |
| 5,703,633 A | 12/1997 | Gehrer et al. |
| 5,743,251 A | 4/1998 | Howell et al. |
| 5,819,756 A | 10/1998 | Mielordt |
| 5,865,185 A | 2/1999 | Collins et al. |
| 5,865,186 A | 2/1999 | Volsey |
| 5,894,841 A | 4/1999 | Voges |
| 5,996,589 A | 12/1999 | St. Charles |
| 6,026,820 A | 2/2000 | Baggett et al. |
| 6,040,560 A | 3/2000 | Fleischhauer et al. |
| 6,062,213 A | 5/2000 | Fuisz et al. |
| 6,090,082 A | 7/2000 | King et al. |
| 6,125,853 A | 10/2000 | Susa et al. |
| 6,155,268 A | 12/2000 | Takeuchi |
| 6,196,218 B1 | 3/2001 | Voges |
| 6,234,167 B1 | 5/2001 | Cox et al. |
| 6,322,268 B1 | 11/2001 | Kaufmann et al. |
| 6,443,146 B1 | 9/2002 | Voges |
| 6,471,782 B1 | 10/2002 | Fang et al. |
| 6,501,052 B2 | 12/2002 | Cox et al. |
| 6,516,796 B1 | 2/2003 | Cox et al. |
| 6,532,965 B1 | 3/2003 | Abhulimen et al. |
| 6,598,607 B2 | 7/2003 | Adiga et al. |
| 6,603,924 B2 | 8/2003 | Brown et al. |
| 6,620,659 B2 | 9/2003 | Emmma et al. |
| 6,701,921 B2 | 3/2004 | Sprinkel, Jr. et al. |
| 6,708,846 B1 | 3/2004 | Fuchs et al. |
| 6,719,443 B2 | 4/2004 | Gutstein et al. |
| 6,722,763 B1 | 4/2004 | Hsu et al. |
| 6,772,756 B2 | 8/2004 | Shayan |
| 7,059,307 B2 | 6/2006 | Pellizzari et al. |
| D531,180 S | 10/2006 | Goto |
| 7,143,766 B2 | 12/2006 | Schuster et al. |
| 7,173,222 B2 | 2/2007 | Cox et al. |
| 7,318,435 B2 | 1/2008 | Pentafragas |
| D590,990 S | 4/2009 | Hon |
| 7,530,352 B2 | 5/2009 | Childers et al. |
| 7,726,320 B2 | 6/2010 | Robinson et al. |
| D624,238 S | 9/2010 | Turner |
| 7,802,569 B2 | 9/2010 | Yeates et al. |
| 7,913,688 B2 | 3/2011 | Cross et al. |
| D642,330 S | 7/2011 | Turner |
| D644,375 S | 8/2011 | Zhou |
| D645,816 S | 9/2011 | Sasada et al. |
| 8,042,550 B2 | 10/2011 | Urtsev et al. |
| 8,205,622 B2 | 6/2012 | Pan |
| 8,251,060 B2 | 8/2012 | White et al. |
| D675,777 S | 2/2013 | Wu |
| 8,365,742 B2 | 2/2013 | Hon |
| 8,371,310 B2 | 2/2013 | Brenneise |
| 8,375,957 B2 | 2/2013 | Hon |
| 8,393,331 B2 | 3/2013 | Hon |
| 8,402,976 B2 | 3/2013 | Fernando et al. |
| 8,479,747 B2 | 7/2013 | Oconnell |
| 8,490,628 B2 | 7/2013 | Hon |
| 8,495,998 B2 | 7/2013 | Schennum |
| D688,415 S | 8/2013 | Kim |
| 8,499,766 B1 | 8/2013 | Newton |
| 8,522,776 B2 | 9/2013 | Wright et al. |
| 8,539,959 B1 | 9/2013 | Scatterday |
| D693,053 S | 11/2013 | Chen |
| D693,765 S | 11/2013 | Workman et al. |
| 8,578,942 B2 | 11/2013 | Schennum |
| D695,450 S | 12/2013 | Benassayag et al. |
| D702,876 S | 4/2014 | Liu |
| 8,689,805 B2 | 4/2014 | Hon |
| D704,634 S | 5/2014 | Eidelman et al. |
| 8,714,161 B2 | 5/2014 | Liu |
| 8,752,545 B2 | 6/2014 | Buchberger |
| 8,752,557 B2 | 6/2014 | Lipowicz |
| 8,757,169 B2 | 6/2014 | Gysland |
| 8,770,187 B2 | 7/2014 | Murphy |
| 8,781,307 B2 | 7/2014 | Buzzetti |
| 8,794,231 B2 | 8/2014 | Thorens et al. |
| 8,813,759 B1 | 8/2014 | Horian |
| 8,857,446 B2 | 10/2014 | Wu |
| 8,869,792 B1 | 10/2014 | Lee |
| D718,492 S | 11/2014 | Albanese |
| 8,881,737 B2 | 11/2014 | Collett et al. |
| 8,893,726 B2 | 11/2014 | Hon |
| D720,094 S | 12/2014 | Alima |
| D720,095 S | 12/2014 | Alima |
| D720,496 S | 12/2014 | Alima |
| D720,497 S | 12/2014 | Alima |
| 8,899,240 B2 | 12/2014 | Mass |
| 8,905,040 B2 | 12/2014 | Scatterday et al. |
| 8,910,639 B2 | 12/2014 | Chang et al. |
| 8,910,640 B2 | 12/2014 | Sears et al. |
| 8,910,641 B2 | 12/2014 | Hon |

(56) References Cited

U.S. PATENT DOCUMENTS

| | | |
|---|---|---|
| D720,881 S | 1/2015 | Liu |
| D720,882 S | 1/2015 | Albanese |
| D720,883 S | 1/2015 | Albanese |
| D721,202 S | 1/2015 | Liu |
| D722,166 S | 2/2015 | Buehl et al. |
| D722,956 S | 2/2015 | Alima |
| 8,948,578 B2 | 2/2015 | Buchberger |
| 8,950,395 B2 | 2/2015 | Schennum |
| 8,955,522 B1 | 2/2015 | Bowen et al. |
| D724,263 S | 3/2015 | Malhi |
| D724,782 S | 3/2015 | Wu |
| D725,310 S | 3/2015 | Eksouzian |
| 8,975,764 B1 | 3/2015 | Abehasera |
| 8,978,663 B2 | 3/2015 | Newton |
| 8,991,402 B2 | 3/2015 | Bowen et al. |
| D726,364 S | 4/2015 | Weigensberg |
| 9,004,073 B2 | 4/2015 | Tucker et al. |
| 9,016,274 B1 | 4/2015 | White |
| D728,855 S | 5/2015 | Liu |
| D729,441 S | 5/2015 | Hua |
| 9,022,026 B2 | 5/2015 | Fang |
| 9,038,642 B2 | 5/2015 | Liu |
| D732,733 S | 6/2015 | Spagnolo et al. |
| 9,046,278 B2 | 6/2015 | Kller |
| 9,055,617 B2 | 6/2015 | Thorens et al. |
| 9,055,770 B2 | 6/2015 | Liu |
| 9,060,388 B2 | 6/2015 | Liu |
| 9,072,321 B2 | 7/2015 | Liu |
| 9,072,322 B2 | 7/2015 | Liu |
| 9,078,472 B2 | 7/2015 | Liu |
| 9,078,474 B2 | 7/2015 | Thompson |
| 9,078,475 B2 | 7/2015 | Li et al. |
| 9,089,168 B2 | 7/2015 | Liu |
| 9,095,175 B2 | 8/2015 | Terry et al. |
| 9,101,729 B2 | 8/2015 | Liu |
| 9,113,659 B2 | 8/2015 | Liu |
| 9,131,733 B2 | 9/2015 | Liu |
| 9,167,852 B2 | 10/2015 | Xiu |
| D743,099 S | 11/2015 | Oglesby |
| 9,185,937 B2 | 11/2015 | Liu |
| 9,197,726 B2 | 11/2015 | Stanimirovic et al. |
| 9,198,463 B2 | 12/2015 | Liu |
| 9,198,464 B2 | 12/2015 | Liu |
| 9,204,670 B2 | 12/2015 | Liu |
| 9,220,302 B2 | 12/2015 | Depiano et al. |
| 9,220,303 B2 | 12/2015 | Li et al. |
| 9,220,304 B2 | 12/2015 | Greim |
| D747,546 S | 1/2016 | Liu |
| 9,226,525 B2 | 1/2016 | Liu |
| 9,226,526 B2 | 1/2016 | Liu |
| 9,247,773 B2 | 2/2016 | Memari et al. |
| 9,254,002 B2 | 2/2016 | Chong et al. |
| 9,254,007 B2 | 2/2016 | Liu |
| D750,835 S | 3/2016 | Wei |
| 9,271,529 B2 | 3/2016 | Alima |
| 9,277,768 B2 | 3/2016 | Xiu |
| 9,277,769 B2 | 3/2016 | Liu |
| 9,282,773 B2 | 3/2016 | Greim et al. |
| 9,289,014 B2 | 3/2016 | Tucker et al. |
| 9,295,286 B2 | 3/2016 | Shin |
| D754,917 S | 4/2016 | Salem |
| 9,301,549 B2 | 4/2016 | Liu |
| 9,308,336 B2 | 4/2016 | Newton |
| 9,312,687 B2 | 4/2016 | Xiang |
| 9,315,890 B1 | 4/2016 | Frick et al. |
| 9,326,547 B2 | 5/2016 | Tucker et al. |
| 9,332,787 B2 | 5/2016 | Liu |
| 9,345,269 B2 | 5/2016 | Liu |
| 9,345,541 B2 | 5/2016 | Greeley et al. |
| 9,351,522 B2 | 5/2016 | Safari |
| 9,364,800 B2 | 6/2016 | Dubief |
| 9,379,364 B2 | 6/2016 | Alima |
| 9,386,805 B2 | 7/2016 | Liu |
| 9,414,627 B2 | 8/2016 | Liu |
| 9,414,628 B2 | 8/2016 | Liu |
| 9,420,829 B2 | 8/2016 | Thorens et al. |
| 9,420,831 B2 | 8/2016 | Liu |
| 9,423,152 B2 | 8/2016 | Ampolini et al. |
| 9,427,022 B2 | 8/2016 | Levin et al. |
| 9,427,023 B2 | 8/2016 | Liu |
| 9,427,024 B2 | 8/2016 | Liu |
| 9,427,025 B2 | 8/2016 | Liu |
| 9,427,026 B2 | 8/2016 | Wu |
| 9,439,456 B2 | 9/2016 | Liu |
| 9,451,790 B2 | 9/2016 | Liu |
| 9,451,793 B2 | 9/2016 | Zhou |
| 9,456,632 B2 | 10/2016 | Hon |
| 9,456,633 B2 | 10/2016 | Liu |
| 9,459,021 B2 | 10/2016 | Greim et al. |
| 9,462,832 B2 | 10/2016 | Lord |
| 9,474,305 B2 | 10/2016 | Liu |
| 9,480,285 B2 | 11/2016 | Liu |
| 9,480,286 B2 | 11/2016 | Liu |
| 9,497,994 B2 | 11/2016 | Liu |
| 9,497,995 B2 | 11/2016 | Liu |
| 9,497,997 B2 | 11/2016 | Wu |
| 9,497,998 B2 | 11/2016 | Chen |
| 9,497,999 B2 | 11/2016 | Lord |
| 9,498,588 B2 | 11/2016 | Benassayag et al. |
| 9,504,279 B2 | 11/2016 | Chen |
| 9,510,624 B2 | 12/2016 | Li et al. |
| 9,516,898 B2 | 12/2016 | Liu |
| 9,521,867 B2 | 12/2016 | Xiang |
| 9,526,272 B2 | 12/2016 | Liu |
| 9,526,273 B2 | 12/2016 | Liu |
| D776,337 S | 1/2017 | Levin et al. |
| 9,532,598 B2 | 1/2017 | Liu |
| 9,532,599 B2 | 1/2017 | Liu |
| 9,532,601 B2 | 1/2017 | Liu |
| 9,532,602 B2 | 1/2017 | Liu |
| 9,538,781 B2 | 1/2017 | Zheng |
| 9,538,787 B2 | 1/2017 | Liu |
| 9,538,789 B2 | 1/2017 | Liu |
| 9,549,572 B2 | 1/2017 | Dincer et al. |
| 9,549,573 B2 | 1/2017 | Monsees et al. |
| 9,554,596 B2 | 1/2017 | Liu |
| 9,554,597 B2 | 1/2017 | Liu |
| 9,555,203 B2 | 1/2017 | Terry et al. |
| 9,560,882 B2 | 2/2017 | Xiang |
| 9,572,372 B2 | 2/2017 | Liu |
| 9,572,373 B2 | 2/2017 | Chen |
| 9,578,898 B2 | 2/2017 | Liu |
| 9,591,876 B2 | 3/2017 | Alima |
| 9,596,881 B2 | 3/2017 | Chiolini et al. |
| 9,596,884 B2 | 3/2017 | Liu |
| 9,596,886 B2 | 3/2017 | Liu |
| 9,603,386 B2 | 3/2017 | Xiang |
| 9,603,387 B2 | 3/2017 | Liu |
| 9,603,389 B2 | 3/2017 | Chen |
| 9,609,893 B2 | 4/2017 | Novak et al. |
| 9,615,605 B2 | 4/2017 | Liu |
| 9,615,607 B2 | 4/2017 | Liu |
| 9,622,511 B2 | 4/2017 | Zhu |
| 9,627,661 B2 | 4/2017 | Liu |
| 9,629,391 B2 | 4/2017 | Dube et al. |
| 9,629,394 B2 | 4/2017 | Aronie et al. |
| 9,635,886 B2 | 5/2017 | Tu |
| 9,642,396 B2 | 5/2017 | Liu |
| 9,645,134 B1 | 5/2017 | Farmen et al. |
| 9,648,905 B2 | 5/2017 | Levitz et al. |
| 9,668,517 B2 | 6/2017 | Liu |
| 9,675,108 B2 | 6/2017 | Liu |
| 9,675,113 B2 | 6/2017 | Liu |
| 9,675,114 B2 | 6/2017 | Timmermans |
| 9,675,116 B2 | 6/2017 | Liu |
| 9,675,117 B2 | 6/2017 | Li et al. |
| 9,681,687 B2 | 6/2017 | Liu |
| 9,682,204 B2 | 6/2017 | Matsumoto et al. |
| 9,687,027 B2 | 6/2017 | Poston et al. |
| 9,687,028 B2 | 6/2017 | Park |
| 9,693,586 B2 | 7/2017 | Liu |
| 9,693,587 B2 | 7/2017 | Plojoux et al. |
| 9,695,033 B1 | 7/2017 | Alshouse et al. |
| 9,700,074 B2 | 7/2017 | Liu |

(56) References Cited

U.S. PATENT DOCUMENTS

| | | |
|---|---|---|
| 9,700,075 B2 | 7/2017 | Liu |
| 9,700,076 B2 | 7/2017 | Xiang |
| 9,717,274 B2 | 8/2017 | Daehne et al. |
| 9,717,275 B2 | 8/2017 | Liu |
| 9,717,276 B2 | 8/2017 | Brammer et al. |
| 9,723,872 B2 | 8/2017 | Liu |
| 9,723,873 B2 | 8/2017 | Liu |
| 9,723,874 B2 | 8/2017 | Liu |
| 9,723,875 B2 | 8/2017 | Liu |
| 9,723,876 B2 | 8/2017 | Cadieux et al. |
| 9,730,471 B2 | 8/2017 | Li et al. |
| 9,743,691 B2 | 8/2017 | Minskoff et al. |
| 9,781,953 B2 | 10/2017 | Verleur et al. |
| 9,788,576 B2 | 10/2017 | Liu |
| 9,801,413 B2 | 10/2017 | Zhu |
| 9,814,263 B2 | 11/2017 | Cochand et al. |
| 9,814,265 B2 | 11/2017 | Rinker et al. |
| 9,844,234 B2 | 12/2017 | Thorens et al. |
| 9,918,496 B2 | 3/2018 | Kane et al. |
| 9,974,743 B2 | 5/2018 | Rose et al. |
| 9,999,250 B2 | 6/2018 | Minskoff et al. |
| 10,039,321 B2 | 8/2018 | Verleur et al. |
| 10,058,122 B2 | 8/2018 | Steingraber et al. |
| 10,058,124 B2 | 8/2018 | Monsees et al. |
| 10,085,481 B2 | 10/2018 | Verleur et al. |
| 10,143,233 B2 | 12/2018 | Dubief et al. |
| 2002/0043262 A1 | 4/2002 | Langford et al. |
| 2002/0078951 A1 | 6/2002 | Nichols et al. |
| 2002/0088469 A1 | 7/2002 | Rennecamp |
| 2003/0226837 A1 | 12/2003 | Blake et al. |
| 2004/0050382 A1 | 3/2004 | Goodchild |
| 2004/0200488 A1 | 10/2004 | Felter et al. |
| 2005/0016550 A1 | 1/2005 | Katase |
| 2005/0017685 A1 | 1/2005 | Rees et al. |
| 2005/0134215 A1* | 6/2005 | Bozzone ............... H02J 7/0044 320/112 |
| 2005/0172976 A1 | 8/2005 | Newman et al. |
| 2006/0016453 A1 | 1/2006 | Kim |
| 2006/0093977 A1 | 5/2006 | Pellizzari et al. |
| 2006/0191546 A1 | 8/2006 | Takano et al. |
| 2007/0045288 A1 | 3/2007 | Nelson |
| 2007/0074734 A1 | 4/2007 | Braunshteyn et al. |
| 2007/0229025 A1 | 10/2007 | Tsai et al. |
| 2007/0277816 A1 | 12/2007 | Morrison et al. |
| 2007/0283972 A1 | 12/2007 | Monsees et al. |
| 2008/0023003 A1 | 1/2008 | Rosenthal |
| 2008/0029095 A1 | 2/2008 | Esser |
| 2008/0257367 A1 | 10/2008 | Paterno et al. |
| 2008/0302374 A1 | 12/2008 | Wengert et al. |
| 2009/0095287 A1 | 4/2009 | Emarlou |
| 2009/0133691 A1 | 5/2009 | Yamada et al. |
| 2009/0188490 A1 | 7/2009 | Han |
| 2009/0255534 A1 | 10/2009 | Paterno |
| 2009/0293892 A1 | 12/2009 | Williams et al. |
| 2009/0302019 A1 | 12/2009 | Selenski et al. |
| 2010/0031968 A1 | 2/2010 | Sheikh et al. |
| 2010/0163063 A1 | 7/2010 | Fernando et al. |
| 2010/0194337 A1* | 8/2010 | Opolka ................. H01R 13/22 320/114 |
| 2010/0200008 A1 | 8/2010 | Taieb |
| 2010/0207576 A1* | 8/2010 | Elizalde Rodarte .. H02J 7/0044 320/115 |
| 2010/0253279 A1* | 10/2010 | Matthias ................ B25F 5/00 320/106 |
| 2010/0307518 A1 | 12/2010 | Wang |
| 2011/0036346 A1 | 2/2011 | Cohen et al. |
| 2011/0041861 A1 | 2/2011 | Sebastian et al. |
| 2011/0159705 A1* | 6/2011 | Schmidt ................. H01R 11/30 439/39 |
| 2011/0192397 A1 | 8/2011 | Saskar et al. |
| 2011/0220234 A1 | 9/2011 | Haas |
| 2011/0226236 A1 | 9/2011 | Buchberger |
| 2011/0226266 A1 | 9/2011 | Tao |
| 2011/0265806 A1 | 11/2011 | Alarcon et al. |
| 2011/0277761 A1 | 11/2011 | Terry et al. |
| 2011/0278189 A1 | 11/2011 | Terry et al. |
| 2011/0290248 A1 | 12/2011 | Schennum |
| 2011/0303231 A1 | 12/2011 | Li et al. |
| 2012/0018529 A1 | 1/2012 | Gammon et al. |
| 2012/0048266 A1 | 3/2012 | Alelov |
| 2012/0111346 A1 | 5/2012 | Rinker et al. |
| 2012/0111347 A1 | 5/2012 | Hon |
| 2012/0118301 A1 | 5/2012 | Montaser |
| 2012/0118307 A1 | 5/2012 | Tu |
| 2012/0125353 A1 | 5/2012 | Wollin |
| 2012/0174914 A1 | 7/2012 | Pirshafiey et al. |
| 2012/0199146 A1 | 8/2012 | Marangos |
| 2012/0199663 A1 | 8/2012 | Qiu |
| 2012/0211015 A1 | 8/2012 | Li et al. |
| 2012/0223673 A1* | 9/2012 | Chen .................. H02J 7/0054 320/108 |
| 2012/0234315 A1 | 9/2012 | Li et al. |
| 2012/0255546 A1 | 10/2012 | Goetz et al. |
| 2012/0260926 A1 | 10/2012 | Tu et al. |
| 2012/0260927 A1 | 10/2012 | Liu |
| 2012/0291791 A1 | 11/2012 | Pradeep |
| 2012/0312313 A1 | 12/2012 | Frija |
| 2012/0318882 A1 | 12/2012 | Abehasera |
| 2012/0325227 A1 | 12/2012 | Robinson et al. |
| 2013/0008457 A1 | 1/2013 | Zheng et al. |
| 2013/0014755 A1 | 1/2013 | Kumar et al. |
| 2013/0014772 A1 | 1/2013 | Liu |
| 2013/0025609 A1 | 1/2013 | Liu |
| 2013/0037041 A1* | 2/2013 | Worm ................... A24F 47/008 131/329 |
| 2013/0042865 A1 | 2/2013 | Monsees et al. |
| 2013/0056013 A1 | 3/2013 | Terry et al. |
| 2013/0068239 A1 | 3/2013 | Youn |
| 2013/0087160 A1 | 4/2013 | Gherghe |
| 2013/0104916 A1 | 5/2013 | Bellinger et al. |
| 2013/0152922 A1 | 6/2013 | Benassayag et al. |
| 2013/0152954 A1 | 6/2013 | Youn |
| 2013/0168880 A1* | 7/2013 | Duke ................... A24F 47/008 261/78.2 |
| 2013/0174842 A1 | 7/2013 | Young et al. |
| 2013/0180533 A1 | 7/2013 | Kim et al. |
| 2013/0182421 A1 | 7/2013 | Popper et al. |
| 2013/0192617 A1 | 8/2013 | Thompson |
| 2013/0192618 A1 | 8/2013 | Li et al. |
| 2013/0192623 A1 | 8/2013 | Tucker et al. |
| 2013/0199528 A1 | 8/2013 | Goodman et al. |
| 2013/0213418 A1 | 8/2013 | Tucker et al. |
| 2013/0213420 A1 | 8/2013 | Hon |
| 2013/0220315 A1 | 8/2013 | Conley et al. |
| 2013/0228191 A1 | 9/2013 | Newton |
| 2013/0253433 A1 | 9/2013 | Senior et al. |
| 2013/0255675 A1 | 10/2013 | Liu |
| 2013/0255702 A1 | 10/2013 | Griffith et al. |
| 2013/0276802 A1 | 10/2013 | Scatterday |
| 2013/0284190 A1 | 10/2013 | Scatterday et al. |
| 2013/0284192 A1 | 10/2013 | Peleg et al. |
| 2013/0288081 A1 | 10/2013 | Cheng et al. |
| 2013/0298905 A1 | 11/2013 | Levin et al. |
| 2013/0306084 A1 | 11/2013 | Flick |
| 2013/0312742 A1 | 11/2013 | Monsees et al. |
| 2013/0319431 A1 | 12/2013 | Cyphert et al. |
| 2013/0319435 A1 | 12/2013 | Flick |
| 2013/0319439 A1 | 12/2013 | Gorelick et al. |
| 2013/0319440 A1 | 12/2013 | Capuano |
| 2013/0323941 A1 | 12/2013 | Zeliff et al. |
| 2013/0333711 A1* | 12/2013 | Liu ....................... A24F 47/002 131/329 |
| 2013/0336358 A1 | 12/2013 | Liu |
| 2013/0340775 A1 | 12/2013 | Juster et al. |
| 2014/0000638 A1 | 1/2014 | Sebastian et al. |
| 2014/0014124 A1* | 1/2014 | Glasberg ............... A24F 47/008 131/328 |
| 2014/0014126 A1 | 1/2014 | Peleg et al. |
| 2014/0034070 A1 | 2/2014 | Schennum |
| 2014/0034071 A1 | 2/2014 | Levitz et al. |
| 2014/0041655 A1 | 2/2014 | Barron et al. |
| 2014/0048086 A1 | 2/2014 | Zhanghua |
| 2014/0053856 A1 | 2/2014 | Liu |

(56) References Cited

U.S. PATENT DOCUMENTS

| | | |
|---|---|---|
| 2014/0053857 A1* | 2/2014 | Liu .................. A24F 47/008 131/329 |
| 2014/0060529 A1 | 3/2014 | Zhang |
| 2014/0060552 A1 | 3/2014 | Cohen |
| 2014/0060556 A1 | 3/2014 | Liu |
| 2014/0069425 A1 | 3/2014 | Zhang |
| 2014/0083442 A1 | 3/2014 | Scatterday |
| 2014/0096781 A1 | 4/2014 | Sears et al. |
| 2014/0096782 A1 | 4/2014 | Ampolini et al. |
| 2014/0107815 A1 | 4/2014 | Lamothe |
| 2014/0109898 A1 | 4/2014 | Li et al. |
| 2014/0109921 A1 | 4/2014 | Chen |
| 2014/0116455 A1 | 5/2014 | Youn |
| 2014/0123989 A1 | 5/2014 | Lamothe |
| 2014/0130817 A1 | 5/2014 | Li et al. |
| 2014/0144453 A1 | 5/2014 | Capuano et al. |
| 2014/0150783 A1 | 6/2014 | Liu |
| 2014/0150784 A1 | 6/2014 | Liu |
| 2014/0150785 A1 | 6/2014 | Malik et al. |
| 2014/0150810 A1 | 6/2014 | Hon |
| 2014/0158129 A1 | 6/2014 | Pratt et al. |
| 2014/0166028 A1 | 6/2014 | Fuisz et al. |
| 2014/0166030 A1 | 6/2014 | Li et al. |
| 2014/0174458 A1 | 6/2014 | Katz |
| 2014/0174459 A1 | 6/2014 | Burstyn |
| 2014/0175081 A1 | 6/2014 | Hwa |
| 2014/0182609 A1 | 7/2014 | Liu |
| 2014/0182610 A1* | 7/2014 | Liu .................. A24F 47/008 131/329 |
| 2014/0182612 A1 | 7/2014 | Chen |
| 2014/0190477 A1 | 7/2014 | Qiu |
| 2014/0190496 A1 | 7/2014 | Wensley et al. |
| 2014/0196733 A1 | 7/2014 | Liu |
| 2014/0202454 A1 | 7/2014 | Buchberger |
| 2014/0202474 A1 | 7/2014 | Peleg et al. |
| 2014/0202477 A1 | 7/2014 | Qi et al. |
| 2014/0209106 A1 | 7/2014 | Liu |
| 2014/0209107 A1 | 7/2014 | Liu |
| 2014/0209108 A1 | 7/2014 | Li et al. |
| 2014/0209109 A1 | 7/2014 | Larson |
| 2014/0216450 A1 | 8/2014 | Liu |
| 2014/0216484 A1 | 8/2014 | Liu |
| 2014/0224244 A1 | 8/2014 | Liu |
| 2014/0224267 A1 | 8/2014 | Levitz et al. |
| 2014/0230835 A1 | 8/2014 | Saliman |
| 2014/0238421 A1 | 8/2014 | Shapiro |
| 2014/0238422 A1 | 8/2014 | Plunkett et al. |
| 2014/0238423 A1 | 8/2014 | Tucker et al. |
| 2014/0238424 A1 | 8/2014 | Macko et al. |
| 2014/0246031 A1 | 9/2014 | Liu |
| 2014/0251356 A1 | 9/2014 | Xiang |
| 2014/0253144 A1 | 9/2014 | Novak et al. |
| 2014/0261474 A1 | 9/2014 | Gonda |
| 2014/0261479 A1 | 9/2014 | Xu et al. |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261490 A1 | 9/2014 | Kane |
| 2014/0261492 A1 | 9/2014 | Kane et al. |
| 2014/0261493 A1 | 9/2014 | Smith et al. |
| 2014/0261494 A1 | 9/2014 | Scatterday |
| 2014/0261499 A1 | 9/2014 | Hon |
| 2014/0270729 A1 | 9/2014 | Depiano et al. |
| 2014/0270730 A1 | 9/2014 | Depiano et al. |
| 2014/0278250 A1 | 9/2014 | Smith et al. |
| 2014/0278258 A1 | 9/2014 | Shafer |
| 2014/0283823 A1 | 9/2014 | Liu |
| 2014/0283855 A1 | 9/2014 | Hawes et al. |
| 2014/0283856 A1 | 9/2014 | Xiang |
| 2014/0283859 A1 | 9/2014 | Minskoff et al. |
| 2014/0290676 A1 | 10/2014 | Liu |
| 2014/0290677 A1 | 10/2014 | Liu |
| 2014/0299137 A1 | 10/2014 | Kieckbusch et al. |
| 2014/0299138 A1 | 10/2014 | Xiang |
| 2014/0299141 A1 | 10/2014 | Flick |
| 2014/0301721 A1 | 10/2014 | Ruscio et al. |
| 2014/0305450 A1 | 10/2014 | Xiang |
| 2014/0305451 A1 | 10/2014 | Liu |
| 2014/0311503 A1 | 10/2014 | Liu |
| 2014/0321837 A1 | 10/2014 | Flick |
| 2014/0332017 A1 | 11/2014 | Liu |
| 2014/0332022 A1 | 11/2014 | Li et al. |
| 2014/0334802 A1 | 11/2014 | Dubief |
| 2014/0334803 A1 | 11/2014 | Li et al. |
| 2014/0334804 A1 | 11/2014 | Choi |
| 2014/0338680 A1 | 11/2014 | Abramov et al. |
| 2014/0338684 A1 | 11/2014 | Liu |
| 2014/0338685 A1 | 11/2014 | Amir |
| 2014/0345606 A1 | 11/2014 | Talon |
| 2014/0345631 A1 | 11/2014 | Bowen et al. |
| 2014/0345632 A1 | 11/2014 | Scatterday |
| 2014/0345633 A1 | 11/2014 | Talon et al. |
| 2014/0345635 A1 | 11/2014 | Rabinowitz et al. |
| 2014/0352707 A1 | 12/2014 | Liu |
| 2014/0353856 A1 | 12/2014 | Dubief |
| 2014/0355969 A1 | 12/2014 | Stern |
| 2014/0360516 A1 | 12/2014 | Liu |
| 2014/0366895 A1 | 12/2014 | Li et al. |
| 2014/0366896 A1 | 12/2014 | Li et al. |
| 2014/0366898 A1 | 12/2014 | Monsees et al. |
| 2014/0373833 A1 | 12/2014 | Liu |
| 2014/0376895 A1 | 12/2014 | Han |
| 2014/0378790 A1 | 12/2014 | Cohen |
| 2015/0000682 A1 | 1/2015 | Liu |
| 2015/0007834 A1 | 1/2015 | Liu |
| 2015/0007836 A1 | 1/2015 | Li et al. |
| 2015/0013692 A1 | 1/2015 | Liu |
| 2015/0013695 A1 | 1/2015 | Mcneal et al. |
| 2015/0013700 A1 | 1/2015 | Liu |
| 2015/0013701 A1 | 1/2015 | Liu |
| 2015/0013702 A1 | 1/2015 | Liu |
| 2015/0020822 A1 | 1/2015 | Janardhan et al. |
| 2015/0020823 A1 | 1/2015 | Lipowicz et al. |
| 2015/0020825 A1 | 1/2015 | Galloway et al. |
| 2015/0020829 A1 | 1/2015 | Li |
| 2015/0020830 A1 | 1/2015 | Koller |
| 2015/0020831 A1* | 1/2015 | Weigensberg ........ A24F 47/008 131/329 |
| 2015/0027454 A1 | 1/2015 | Li et al. |
| 2015/0027455 A1 | 1/2015 | Peleg et al. |
| 2015/0027456 A1 | 1/2015 | Janardhan et al. |
| 2015/0027457 A1 | 1/2015 | Janardhan et al. |
| 2015/0027467 A1 | 1/2015 | Liu |
| 2015/0027468 A1 | 1/2015 | Li et al. |
| 2015/0027469 A1 | 1/2015 | Tucker et al. |
| 2015/0027471 A1 | 1/2015 | Feldman et al. |
| 2015/0027472 A1 | 1/2015 | Amir |
| 2015/0027473 A1 | 1/2015 | Graf |
| 2015/0034102 A1 | 2/2015 | Faramarzian |
| 2015/0034103 A1 | 2/2015 | Hon |
| 2015/0034104 A1 | 2/2015 | Zhou |
| 2015/0034106 A1 | 2/2015 | Liu |
| 2015/0040925 A1 | 2/2015 | Saleem et al. |
| 2015/0040929 A1 | 2/2015 | Hon |
| 2015/0047658 A1 | 2/2015 | Cyphert et al. |
| 2015/0047661 A1 | 2/2015 | Blackley et al. |
| 2015/0047662 A1 | 2/2015 | Hopps |
| 2015/0047663 A1 | 2/2015 | Liu |
| 2015/0053215 A1 | 2/2015 | Liu |
| 2015/0053220 A1 | 2/2015 | Levy et al. |
| 2015/0059783 A1 | 3/2015 | Liu |
| 2015/0059787 A1 | 3/2015 | Qiu |
| 2015/0075545 A1 | 3/2015 | Xiang |
| 2015/0078735 A1 | 3/2015 | Cormack |
| 2015/0083145 A1 | 3/2015 | Li et al. |
| 2015/0083147 A1 | 3/2015 | Schiff et al. |
| 2015/0090253 A1 | 4/2015 | Farrow |
| 2015/0090256 A1 | 4/2015 | Chung |
| 2015/0090278 A1 | 4/2015 | Schiff et al. |
| 2015/0090281 A1 | 4/2015 | Chen |
| 2015/0091501 A1 | 4/2015 | Claudepierre |
| 2015/0101623 A1 | 4/2015 | Liu |
| 2015/0101625 A1 | 4/2015 | Newton et al. |
| 2015/0101626 A1 | 4/2015 | Li et al. |

(56) References Cited

U.S. PATENT DOCUMENTS

| | | |
|---|---|---|
| 2015/0107609 A1 | 4/2015 | Liu |
| 2015/0107611 A1 | 4/2015 | Metrangolo et al. |
| 2015/0114407 A1 | 4/2015 | Duncan et al. |
| 2015/0114410 A1 | 4/2015 | Doster |
| 2015/0118895 A1 | 4/2015 | Zheng et al. |
| 2015/0122252 A1 | 5/2015 | Frija |
| 2015/0122274 A1 | 5/2015 | Cohen et al. |
| 2015/0128966 A1 | 5/2015 | Lord |
| 2015/0128967 A1 | 5/2015 | Robinson et al. |
| 2015/0128970 A1 | 5/2015 | Liu |
| 2015/0128973 A1 | 5/2015 | Li et al. |
| 2015/0128976 A1 | 5/2015 | Verleur et al. |
| 2015/0128977 A1 | 5/2015 | Li et al. |
| 2015/0136153 A1 | 5/2015 | Lord |
| 2015/0136154 A1 | 5/2015 | Mitrev et al. |
| 2015/0136158 A1 | 5/2015 | Stevens et al. |
| 2015/0141093 A1 | 5/2015 | Sela et al. |
| 2015/0142387 A1 | 5/2015 | Alarcon et al. |
| 2015/0144145 A1 | 5/2015 | Chang et al. |
| 2015/0144147 A1 | 5/2015 | Li et al. |
| 2015/0150303 A1 | 6/2015 | Jensen |
| 2015/0150305 A1 | 6/2015 | Shenkal |
| 2015/0150307 A1 | 6/2015 | Liu |
| 2015/0157053 A1 | 6/2015 | Mayor |
| 2015/0157054 A1 | 6/2015 | Liu |
| 2015/0157055 A1 | 6/2015 | Lord |
| 2015/0163859 A1 | 6/2015 | Schneider et al. |
| 2015/0164138 A1 | 6/2015 | Liu |
| 2015/0164141 A1 | 6/2015 | Newton |
| 2015/0164142 A1 | 6/2015 | Li et al. |
| 2015/0164143 A1 | 6/2015 | Maas |
| 2015/0164144 A1 | 6/2015 | Liu |
| 2015/0164146 A1 | 6/2015 | Li et al. |
| 2015/0164147 A1 | 6/2015 | Verleur et al. |
| 2015/0167976 A1 | 6/2015 | Recio |
| 2015/0173124 A1 | 6/2015 | Qiu |
| 2015/0173421 A1 | 6/2015 | Hsieh |
| 2015/0173422 A1 | 6/2015 | Liu |
| 2015/0181928 A1 | 7/2015 | Liu |
| 2015/0181939 A1 | 7/2015 | Liu |
| 2015/0181940 A1 | 7/2015 | Liu |
| 2015/0181941 A1 | 7/2015 | Liu |
| 2015/0181943 A1 | 7/2015 | Li et al. |
| 2015/0181944 A1 | 7/2015 | Li et al. |
| 2015/0181945 A1 | 7/2015 | Tremblay |
| 2015/0184846 A1 | 7/2015 | Liu |
| 2015/0189695 A1 | 7/2015 | Xiang |
| 2015/0189918 A1 | 7/2015 | Liu |
| 2015/0189919 A1 | 7/2015 | Liu |
| 2015/0189920 A1 | 7/2015 | Liu |
| 2015/0196055 A1 | 7/2015 | Liu |
| 2015/0196056 A1 | 7/2015 | Liu |
| 2015/0196057 A1 | 7/2015 | Wu |
| 2015/0196058 A1 | 7/2015 | Lord |
| 2015/0196059 A1 | 7/2015 | Liu |
| 2015/0196062 A1 | 7/2015 | Li et al. |
| 2015/0201674 A1 | 7/2015 | Dooly et al. |
| 2015/0201675 A1 | 7/2015 | Lord |
| 2015/0208725 A1 | 7/2015 | Tsai |
| 2015/0208726 A1 | 7/2015 | Liu |
| 2015/0208728 A1 | 7/2015 | Lord |
| 2015/0208730 A1 | 7/2015 | Li et al. |
| 2015/0208731 A1 | 7/2015 | Malamud et al. |
| 2015/0216232 A1 | 8/2015 | Bless et al. |
| 2015/0216233 A1 | 8/2015 | Sears et al. |
| 2015/0216234 A1 | 8/2015 | Chung |
| 2015/0216235 A1 | 8/2015 | Liu |
| 2015/0216236 A1 | 8/2015 | Bless et al. |
| 2015/0216237 A1 | 8/2015 | Wensley et al. |
| 2015/0217068 A1 | 8/2015 | Wakalopulos |
| 2015/0223521 A1 | 8/2015 | Menting et al. |
| 2015/0223522 A1 | 8/2015 | Ampolini et al. |
| 2015/0223523 A1 | 8/2015 | Mccullough |
| 2015/0224268 A1 | 8/2015 | Henry et al. |
| 2015/0230521 A1 | 8/2015 | Talon |
| 2015/0237914 A1 | 8/2015 | Han |
| 2015/0237916 A1 | 8/2015 | Farine et al. |
| 2015/0237917 A1 | 8/2015 | Lord |
| 2015/0237918 A1 | 8/2015 | Liu |
| 2015/0245654 A1 | 9/2015 | Memari et al. |
| 2015/0245658 A1 | 9/2015 | Worm et al. |
| 2015/0245659 A1 | 9/2015 | Depiano et al. |
| 2015/0245661 A1 | 9/2015 | Milin |
| 2015/0245665 A1 | 9/2015 | Memari et al. |
| 2015/0245669 A1 | 9/2015 | Cadieux et al. |
| 2015/0282525 A1 | 10/2015 | Plojoux et al. |
| 2015/0282526 A1 | 10/2015 | Wu |
| 2015/0296883 A1 | 10/2015 | Wu |
| 2015/0296885 A1 | 10/2015 | Liu |
| 2015/0296887 A1 | 10/2015 | Zhu |
| 2015/0296888 A1 | 10/2015 | Liu |
| 2015/0305409 A1 | 10/2015 | Verleur et al. |
| 2015/0313284 A1 | 11/2015 | Liu |
| 2015/0342254 A1 | 12/2015 | Mironov et al. |
| 2015/0351455 A1 | 12/2015 | Liu |
| 2015/0351456 A1 | 12/2015 | Johnson et al. |
| 2015/0351457 A1 | 12/2015 | Liu |
| 2016/0000148 A1 | 1/2016 | Liu |
| 2016/0021931 A1 | 1/2016 | Hawes et al. |
| 2016/0021933 A1 | 1/2016 | Thorens et al. |
| 2016/0029697 A1 | 2/2016 | Shafer |
| 2016/0044962 A1 | 2/2016 | Thorens et al. |
| 2016/0044963 A1 | 2/2016 | Saleem |
| 2016/0058071 A1 | 3/2016 | Hearn |
| 2016/0058072 A1 | 3/2016 | Liu |
| 2016/0073690 A1 | 3/2016 | Liu |
| 2016/0073693 A1 | 3/2016 | Reevell |
| 2016/0073694 A1 | 3/2016 | Liu |
| 2016/0081395 A1 | 3/2016 | Thorens et al. |
| 2016/0095352 A1 | 4/2016 | Liu |
| 2016/0095353 A1 | 4/2016 | Liu |
| 2016/0106154 A1 | 4/2016 | Lord |
| 2016/0106155 A1 | 4/2016 | Reevell |
| 2016/0113325 A1 | 4/2016 | Liu |
| 2016/0120218 A1 | 5/2016 | Schennum et al. |
| 2016/0120220 A1 | 5/2016 | Malgat et al. |
| 2016/0120222 A1 | 5/2016 | Bagai et al. |
| 2016/0128384 A1 | 5/2016 | Luciani |
| 2016/0128385 A1 | 5/2016 | Lin |
| 2016/0128388 A1 | 5/2016 | Liu |
| 2016/0128390 A1 | 5/2016 | Liu |
| 2016/0135501 A1 | 5/2016 | Liu |
| 2016/0135503 A1 | 5/2016 | Liu |
| 2016/0143354 A1 | 5/2016 | Liu |
| 2016/0143357 A1 | 5/2016 | Liu |
| 2016/0143359 A1 | 5/2016 | Xiang |
| 2016/0143365 A1 | 5/2016 | Liu |
| 2016/0150821 A1 | 6/2016 | Liu |
| 2016/0150824 A1 | 6/2016 | Memari et al. |
| 2016/0150826 A1 | 6/2016 | Liu |
| 2016/0150827 A1 | 6/2016 | Liu |
| 2016/0157523 A1 | 6/2016 | Liu |
| 2016/0174609 A1 | 6/2016 | Mironov |
| 2016/0183593 A1 | 6/2016 | Liu |
| 2016/0183594 A1 | 6/2016 | Liu |
| 2016/0192705 A1 | 7/2016 | Borkovec et al. |
| 2016/0192706 A1 | 7/2016 | Kananen |
| 2016/0198765 A1 | 7/2016 | Liu |
| 2016/0198766 A1 | 7/2016 | Liu |
| 2016/0198767 A1 | 7/2016 | Verleur |
| 2016/0198768 A1 | 7/2016 | Liu |
| 2016/0198769 A1 | 7/2016 | Liu |
| 2016/0198770 A1 | 7/2016 | Alarcon |
| 2016/0205999 A1 | 7/2016 | Liu |
| 2016/0206000 A1 | 7/2016 | Lord et al. |
| 2016/0213061 A1 | 7/2016 | Liu |
| 2016/0213066 A1 | 7/2016 | Zitzke et al. |
| 2016/0219938 A1 | 8/2016 | Mamoun et al. |
| 2016/0235119 A1 | 8/2016 | Liu |
| 2016/0235120 A1 | 8/2016 | Liu |
| 2016/0235121 A1 | 8/2016 | Rogan et al. |
| 2016/0242463 A1 | 8/2016 | Liu |
| 2016/0242464 A1 | 8/2016 | Liu |
| 2016/0242466 A1 | 8/2016 | Lord et al. |

(56) References Cited

U.S. PATENT DOCUMENTS

| | | |
|---|---|---|
| 2016/0242468 A1 | 8/2016 | Liu |
| 2016/0249680 A1 | 9/2016 | Liu |
| 2016/0249682 A1 | 9/2016 | Leadley et al. |
| 2016/0262449 A1 | 9/2016 | Liu |
| 2016/0262451 A1 | 9/2016 | Liu |
| 2016/0262459 A1 | 9/2016 | Monsees et al. |
| 2016/0270442 A1 | 9/2016 | Liu |
| 2016/0270443 A1 | 9/2016 | Liu |
| 2016/0270444 A1 | 9/2016 | Lin |
| 2016/0270445 A1 | 9/2016 | Liu |
| 2016/0278431 A1 | 9/2016 | Liu |
| 2016/0278432 A1 | 9/2016 | Liu |
| 2016/0278433 A1 | 9/2016 | Xiang |
| 2016/0278434 A1 | 9/2016 | Liu |
| 2016/0278435 A1 | 9/2016 | Choukroun et al. |
| 2016/0278436 A1 | 9/2016 | Verleur et al. |
| 2016/0286856 A1 | 10/2016 | Liu |
| 2016/0286859 A1 | 10/2016 | Liu |
| 2016/0286862 A1 | 10/2016 | Silvetrini |
| 2016/0286863 A1 | 10/2016 | Lin |
| 2016/0286864 A1 | 10/2016 | Lin |
| 2016/0286865 A1 | 10/2016 | King et al. |
| 2016/0295917 A1 | 10/2016 | Malgat et al. |
| 2016/0295918 A1 | 10/2016 | Liu |
| 2016/0295922 A1 | 10/2016 | John et al. |
| 2016/0295923 A1 | 10/2016 | Lin |
| 2016/0295924 A1 | 10/2016 | Liu |
| 2016/0295926 A1 | 10/2016 | Zuber |
| 2016/0302471 A1 | 10/2016 | Bowen et al. |
| 2016/0309779 A1 | 10/2016 | Liu |
| 2016/0309783 A1 | 10/2016 | Hopps et al. |
| 2016/0309784 A1 | 10/2016 | Silvestrini et al. |
| 2016/0309789 A1 | 10/2016 | Thomas |
| 2016/0316818 A1 | 11/2016 | Liu |
| 2016/0316820 A1 | 11/2016 | Liu |
| 2016/0316821 A1 | 11/2016 | Liu |
| 2016/0316822 A1 | 11/2016 | Liu |
| 2016/0324213 A1 | 11/2016 | Liu |
| 2016/0324215 A1 | 11/2016 | Mironov et al. |
| 2016/0331032 A1 | 11/2016 | Malgat et al. |
| 2016/0331033 A1 | 11/2016 | Hopps et al. |
| 2016/0331040 A1 | 11/2016 | Nakano et al. |
| 2016/0338402 A1 | 11/2016 | Buehler et al. |
| 2016/0338405 A1 | 11/2016 | Liu |
| 2016/0338406 A1 | 11/2016 | Liu |
| 2016/0338411 A1 | 11/2016 | Liu |
| 2016/0345625 A1 | 12/2016 | Liu |
| 2016/0345627 A1 | 12/2016 | Liu |
| 2016/0345628 A1 | 12/2016 | Sabet |
| 2016/0345630 A1 | 12/2016 | Mironov et al. |
| 2016/0345634 A1 | 12/2016 | Fernando et al. |
| 2016/0353798 A1 | 12/2016 | Liu |
| 2016/0353804 A1 | 12/2016 | Lord |
| 2016/0360784 A1 | 12/2016 | Liu |
| 2016/0360792 A1 | 12/2016 | Liu |
| 2016/0360793 A1 | 12/2016 | Liu |
| 2016/0366927 A1 | 12/2016 | Liu |
| 2016/0366935 A1 | 12/2016 | Liu |
| 2016/0366936 A1 | 12/2016 | Liu |
| 2016/0366939 A1 | 12/2016 | Alarcon et al. |
| 2016/0366940 A1 | 12/2016 | Liu |
| 2016/0366942 A1 | 12/2016 | Liu |
| 2016/0366947 A1 | 12/2016 | Monsees et al. |
| 2016/0371437 A1 | 12/2016 | Alarcon et al. |
| 2016/0374391 A1 | 12/2016 | Liu |
| 2016/0374392 A1 | 12/2016 | Liu |
| 2016/0374393 A1 | 12/2016 | Chen |
| 2016/0374399 A1 | 12/2016 | Monsees et al. |
| 2017/0006919 A1 | 1/2017 | Liu |
| 2017/0006920 A1 | 1/2017 | Liu |
| 2017/0013885 A1 | 1/2017 | Qiu |
| 2017/0019951 A1 | 1/2017 | Louveau et al. |
| 2017/0020194 A1 | 1/2017 | Rehders |
| 2017/0035111 A1 | 2/2017 | Slurink et al. |
| 2017/0042229 A1 | 2/2017 | Liu |
| 2017/0049152 A1 | 2/2017 | Liu |
| 2017/0055586 A1 | 3/2017 | Liu |
| 2017/0055589 A1 | 3/2017 | Fernando et al. |
| 2017/0071251 A1 | 3/2017 | Goch |
| 2017/0079110 A1 | 3/2017 | Plattner |
| 2017/0079329 A1 | 3/2017 | Zitzke |
| 2017/0099880 A1 | 4/2017 | Hawes |
| 2017/0157341 A1 | 6/2017 | Pandya et al. |
| 2017/0162979 A1 | 6/2017 | Liu |
| 2017/0172207 A1 | 6/2017 | Liu |
| 2017/0188629 A1 | 7/2017 | Dickens et al. |
| 2017/0197046 A1 | 7/2017 | Buchberger |
| 2017/0231281 A1 | 8/2017 | Hatton et al. |
| 2017/0231282 A1 | 8/2017 | Bowen et al. |
| 2017/0233114 A1 | 8/2017 | Christensen et al. |
| 2017/0251719 A1 | 9/2017 | Cyphert et al. |
| 2018/0303169 A1 | 10/2018 | Sears et al. |

FOREIGN PATENT DOCUMENTS

| | | |
|---|---|---|
| AU | 201408287 B2 | 12/2016 |
| AU | 2014208287 B2 | 12/2016 |
| AU | 201702891 B2 | 5/2019 |
| AU | 2017202891 B2 | 5/2019 |
| CA | 2641869 A1 | 5/2010 |
| CA | 2 846 286 A1 | 4/2013 |
| CN | 1233436 A | 11/1999 |
| CN | 201018927 Y | 2/2008 |
| CN | 201104488 Y | 8/2008 |
| CN | 100589726 | 2/2010 |
| CN | 201408820 | 2/2010 |
| CN | 201408820 Y | 2/2010 |
| CN | 201430916 Y | 3/2010 |
| CN | 101861691 | 10/2010 |
| CN | 101869356 A | 10/2010 |
| CN | 201781984 U | 4/2011 |
| CN | 201787984 U | 4/2011 |
| CN | 202004499 U | 10/2011 |
| CN | 102754924 | 10/2012 |
| CN | 202566289 U | 12/2012 |
| CN | 202603608 U | 12/2012 |
| CN | 202890462 U | 4/2013 |
| CN | 202941411 | 5/2013 |
| CN | 202941411 U | 5/2013 |
| CN | 203040683 U | 7/2013 |
| CN | 203087525 U | 7/2013 |
| CN | 203152489 | 8/2013 |
| CN | 203152489 U | 8/2013 |
| CN | 203168035 | 9/2013 |
| CN | 203182012 | 9/2013 |
| CN | 203182012 U | 9/2013 |
| CN | 203182012 U | 9/2013 |
| CN | 203182014 | 9/2013 |
| CN | 103349363 | 10/2013 |
| CN | 203327953 | 12/2013 |
| CN | 102727969 B | 2/2014 |
| CN | 203467677 U | 3/2014 |
| CN | 103750571 A | 4/2014 |
| CN | 203538385 U | 4/2014 |
| CN | 204466899 | 7/2015 |
| DE | 19619536 A1 | 10/1997 |
| DE | 102006004484 A1 | 8/2007 |
| DE | 202012004792 U1 | 6/2012 |
| EP | 0 358 114 A2 | 3/1990 |
| EP | 0 533 599 A1 | 3/1993 |
| EP | 2110033 A1 | 10/1997 |
| EP | 0 845 220 A1 | 6/1998 |
| EP | 2110033 A1 | 10/2009 |
| EP | 2113178 | 11/2009 |
| EP | 2399636 | 12/2011 |
| EP | 2399636 A1 | 12/2011 |
| EP | 2614731 A1 | 7/2013 |
| EP | 2 654 471 B1 | 10/2013 |
| EP | 2654471 | 7/2014 |
| EP | 2862457 A1 | 4/2015 |
| EP | 3023016 A1 | 5/2016 |
| EP | 2967154 B1 | 10/2018 |
| EP | 3456214 | 3/2019 |
| EP | 3469934 | 4/2019 |

(56) References Cited

FOREIGN PATENT DOCUMENTS

| | | |
|---|---|---|
| GB | 2264237 A | 8/1993 |
| GB | 2266466 A | 11/1993 |
| JP | 2001161819 A | 6/2001 |
| JP | 2009213428 A | 9/2009 |
| JP | 2011024430 | 2/2011 |
| KR | 101 011 453 BI | 1/2011 |
| KR | 101011453 | 1/2011 |
| KR | 20110006928 U | 7/2011 |
| KR | 200457340 Y1 | 12/2011 |
| KR | 20120008751 U | 2/2012 |
| KR | 20120113519 A | 10/2012 |
| KR | 20130106741 A | 9/2013 |
| KR | 20130107658 A | 10/2013 |
| KR | 101357574 B1 | 2/2014 |
| TW | 201436722 | 10/2014 |
| TW | 201438608 | 10/2014 |
| WO | 98/17131 A1 | 4/1998 |
| WO | WO0005976 A1 | 2/2000 |
| WO | 02/098390 A2 | 12/2002 |
| WO | 03/000324 A1 | 1/2003 |
| WO | 03/034847 A1 | 5/2003 |
| WO | WO2003061716 A1 | 7/2003 |
| WO | WO2003103387 A2 | 12/2003 |
| WO | WO2004080216 A1 | 9/2004 |
| WO | WO2006021153 A1 | 3/2006 |
| WO | WO2007066374 A1 | 6/2007 |
| WO | 20071078273 A1 | 7/2007 |
| WO | WO2008077271 A1 | 7/2008 |
| WO | WO2008087161 A1 | 7/2008 |
| WO | WO2009003204 A2 | 1/2009 |
| WO | WO2010118644 A1 | 10/2010 |
| WO | WO2010140841 A2 | 12/2010 |
| WO | WO2010145805 A1 | 12/2010 |
| WO | WO2011010334 A1 | 1/2011 |
| WO | WO2011125058 A1 | 10/2011 |
| WO | WO2012043941 A1 | 4/2012 |
| WO | WO2012059726 A2 | 5/2012 |
| WO | WO2012062600 A1 | 5/2012 |
| WO | 20121072762 A1 | 6/2012 |
| WO | WO2012088675 A1 | 7/2012 |
| WO | WO2012091249 A1 | 7/2012 |
| WO | WO2012100523 A1 | 8/2012 |
| WO | WO2012129812 A1 | 10/2012 |
| WO | WO2012134117 A2 | 10/2012 |
| WO | WO2012173322 A1 | 12/2012 |
| WO | WO2012174677 A1 | 12/2012 |
| WO | WO2013012157 A1 | 1/2013 |
| WO | WO2013020220 A1 | 2/2013 |
| WO | 20131034453 A1 | 3/2013 |
| WO | WO2013040193 A2 | 3/2013 |
| WO | WO2013044537 A1 | 4/2013 |
| WO | WO2013068100 A1 | 5/2013 |
| WO | WO2013076750 A1 | 5/2013 |
| WO | 2013/093695 A1 | 6/2013 |
| WO | WO2013083635 A1 | 6/2013 |
| WO | WO2013089358 A1 | 6/2013 |
| WO | WO2013089551 A1 | 6/2013 |
| WO | WO2013093695 | 6/2013 |
| WO | WO2013098397 | 7/2013 |
| WO | 20131116567 A1 | 8/2013 |
| WO | WO2013110208 A1 | 8/2013 |
| WO | WO2013110209 A1 | 8/2013 |
| WO | WO2013110210 A1 | 8/2013 |
| WO | WO2013113173 A1 | 8/2013 |
| WO | WO2013113174 A1 | 8/2013 |
| WO | WO2013113612 A1 | 8/2013 |
| WO | WO2013116983 A1 | 8/2013 |
| WO | WO2013131763 A1 | 9/2013 |
| WO | WO2013142678 A1 | 9/2013 |
| WO | 20131155645 A1 | 10/2013 |
| WO | 20131159245 A1 | 10/2013 |
| WO | WO2013171206 A1 | 11/2013 |
| WO | WO2013174001 A1 | 11/2013 |
| WO | 2014/008646 A1 | 1/2014 |
| WO | WO2014008646 | 1/2014 |
| WO | WO2014020953 A1 | 2/2014 |
| WO | WO2014023171 A1 | 2/2014 |
| WO | WO2014032280 A1 | 3/2014 |
| WO | WO2014040915 A1 | 3/2014 |
| WO | WO2014047948 A1 | 4/2014 |
| WO | WO2014047955 A1 | 4/2014 |
| WO | WO2014071747 A1 | 5/2014 |
| WO | WO2014101119 A1 | 7/2014 |
| WO | WO2014101401 A1 | 7/2014 |
| WO | WO2014101734 A1 | 7/2014 |
| WO | WO2014110750 A1 | 7/2014 |
| WO | WO2014110761 A1 | 7/2014 |
| WO | WO2014113949 A1 | 7/2014 |
| WO | WO2014121509 A1 | 8/2014 |
| WO | WO2014125340 A1 | 8/2014 |
| WO | WO2014127446 A1 | 8/2014 |
| WO | WO2014134781 A1 | 9/2014 |
| WO | WO2014139609 | 9/2014 |
| WO | WO2014146270 A1 | 9/2014 |
| WO | WO2014150979 A2 | 9/2014 |
| WO | WO2014161181 A1 | 10/2014 |
| WO | WO2014166039 A1 | 10/2014 |
| WO | WO2014169437 A1 | 10/2014 |
| WO | WO2014169667 A1 | 10/2014 |
| WO | WO2014186983 A1 | 11/2014 |
| WO | WO2014198042 A1 | 12/2014 |
| WO | WO2014201610 A1 | 12/2014 |
| WO | WO2014201611 A1 | 12/2014 |
| WO | WO2014201666 A1 | 12/2014 |
| WO | WO2014201668 A1 | 12/2014 |
| WO | WO2014205749 A1 | 12/2014 |
| WO | WO2014205780 A1 | 12/2014 |
| WO | WO2014205807 A1 | 12/2014 |
| WO | WO2014206148 A1 | 12/2014 |
| WO | WO2015000125 A1 | 1/2015 |
| WO | WO2015000180 A1 | 1/2015 |
| WO | WO2015003327 A1 | 1/2015 |
| WO | WO2015003372 A1 | 1/2015 |
| WO | WO2015003374 A1 | 1/2015 |
| WO | WO2015006929 A1 | 1/2015 |
| WO | WO2015010242 A1 | 1/2015 |
| WO | WO2015010277 A1 | 1/2015 |
| WO | WO2015010284 A1 | 1/2015 |
| WO | WO2015010291 A1 | 1/2015 |
| WO | WO2015010310 A1 | 1/2015 |
| WO | WO2015010336 A1 | 1/2015 |
| WO | WO2015010345 A1 | 1/2015 |
| WO | WO2015013890 A1 | 2/2015 |
| WO | WO2015013891 A1 | 2/2015 |
| WO | WO2015013892 A1 | 2/2015 |
| WO | WO2015013926 A1 | 2/2015 |
| WO | WO2015013950 A1 | 2/2015 |
| WO | WO2015013967 A1 | 2/2015 |
| WO | WO2015017971 A1 | 2/2015 |
| WO | WO2015018026 A1 | 2/2015 |
| WO | WO2015018120 A1 | 2/2015 |
| WO | WO2015021612 A1 | 2/2015 |
| WO | WO2015021646 A1 | 2/2015 |
| WO | WO2015021651 A1 | 2/2015 |
| WO | WO2015021652 A1 | 2/2015 |
| WO | WO2015021655 A1 | 2/2015 |
| WO | WO2015021658 A1 | 2/2015 |
| WO | WO2015024239 A1 | 2/2015 |
| WO | WO2015024247 A1 | 2/2015 |
| WO | WO2015026081 A1 | 2/2015 |
| WO | WO2015027383 A1 | 3/2015 |
| WO | WO2015027435 A1 | 3/2015 |
| WO | WO2015027436 A1 | 3/2015 |
| WO | WO2015027470 A1 | 3/2015 |
| WO | WO2015032050 A1 | 3/2015 |
| WO | WO2015032055 A1 | 3/2015 |
| WO | WO2015032078 A1 | 3/2015 |
| WO | WO2015032093 A1 | 3/2015 |
| WO | WO2015035510 A1 | 3/2015 |
| WO | WO2015035547 A1 | 3/2015 |
| WO | WO2015035557 A1 | 3/2015 |
| WO | WO2015035587 A1 | 3/2015 |
| WO | WO2015035623 A1 | 3/2015 |
| WO | WO2015035689 A1 | 3/2015 |

(56) References Cited

FOREIGN PATENT DOCUMENTS

| WO | WO2015037925 A1 | 3/2015 |
|---|---|---|
| WO | WO2015039275 A1 | 3/2015 |
| WO | WO2015039280 A1 | 3/2015 |
| WO | WO2015039332 A1 | 3/2015 |
| WO | WO2015042790 A1 | 4/2015 |
| WO | WO2015042811 A1 | 4/2015 |
| WO | WO2015042848 A1 | 4/2015 |
| WO | WO2015042943 A1 | 4/2015 |
| WO | WO2015051509 A1 | 4/2015 |
| WO | WO2015051538 A1 | 4/2015 |
| WO | WO2015054815 A1 | 4/2015 |
| WO | WO2015054862 A1 | 4/2015 |
| WO | WO2015055314 A1 | 4/2015 |
| WO | WO2015058340 A1 | 4/2015 |
| WO | WO2015058387 A1 | 4/2015 |
| WO | WO2015062041 A1 | 5/2015 |
| WO | WO2015066136 A1 | 5/2015 |
| WO | WO2015066927 A1 | 5/2015 |
| WO | WO2015070398 A1 | 5/2015 |
| WO | WO2015070405 A1 | 5/2015 |
| WO | WO2015070405 A2 | 5/2015 |
| WO | WO2015071703 A1 | 5/2015 |
| WO | WO2015074187 A1 | 5/2015 |
| WO | WO2015074265 A1 | 5/2015 |
| WO | WO2015077998 A1 | 6/2015 |
| WO | WO2015077999 A1 | 6/2015 |
| WO | WO2015078010 A1 | 6/2015 |
| WO | WO2015079197 A1 | 6/2015 |
| WO | WO2015082560 | 6/2015 |
| WO | WO2015082560 A1 | 6/2015 |
| WO | WO2015089711 A1 | 6/2015 |
| WO | WO2015106434 A1 | 7/2015 |
| WO | WO2015106440 A1 | 7/2015 |
| WO | WO2015107552 A1 | 7/2015 |
| WO | WO2015109476 A1 | 7/2015 |
| WO | WO2015109532 A1 | 7/2015 |
| WO | WO2015109540 A1 | 7/2015 |
| WO | WO2015109618 A1 | 7/2015 |
| WO | W02015120588 A1 | 8/2015 |
| WO | WO2015117285 A1 | 8/2015 |
| WO | WO2015120588 A1 | 8/2015 |
| WO | WO2015120591 A1 | 8/2015 |
| WO | WO2015120623 A1 | 8/2015 |
| WO | WO2015123831 A1 | 8/2015 |
| WO | WO2014113949 A1 | 7/2017 |

OTHER PUBLICATIONS

Andrus et al., "Nicotine microaerosol inhaler", Canadian Respiratory Journal, Nov./Dec. 1999, pp. 509-512, Vo. 6, No. 6.

"What is a MOSFET, what does it look like, and how does it work?" dated May 24, 2004, printed from the Internet Archive, i.e., the Wayback machine, which was archived on Mar. 5, 2010 ("TechPowerUp").

"What is a MOSFET, what does it look like, and how does it work?" dated May 24, 2004, printed from the Internet Archive i.e., the Wayback machine, which was archived on Jul. 20, 2011 ("TechPowerUp").

European Patent Office, Partial European Search Report dated Oct. 13, 2015 for EP Application No. 14159709.6 filed Mar. 14, 2014.

Office Action issued in counterpart European Application No. 14159710.4, dated Apr. 24, 2017.

"New Tank E-Cigarette:innokin 510T." From China Manufacturer, Manufactory, Factory and Supplier on ECVV.com, Nov. 15, 2011, www.ecvv.com/products/3118191.html.

Cloud pen vaporizer unboxing review by vaporizer blog // VaporizerBlog.com, https://www.youtube.com/watch?v=ixHMkXoWKNg.

Glory Vapes. "Glory Vapes TV: Kanger S1 Cubica Series Starter Kit Unboxing." YouTube, YouTube, Aug. 8, 2013, www.youtube.com/watch?v=NQivJ6YhdbA.

Uptoyou Fromeme. "Newest Elips CCV Pure Flat Shaped Rechargeable Double Electronic Cigarettes E-Cigarette Set." YouTube, Sep. 11, 2013, https://www.youtube.com/watch?v=ZkQe9xztu44.

U.S. Appl. No. 14/196,729, filed Mar. 4, 2014, U.S. Pat. No. 10,039,321.

U.S. Appl. No. 14/539,801, filed Nov. 12, 2014, U.S. Pat. No. 10,085,481.

U.S. Appl. No. 14/790,566, filed Jul. 2, 2015, US20150305409.

U.S. Appl. No. 16/119,359, filed Aug. 31, 2018, US20180368481.

U.S. Appl. No. 16/179,829, filed Nov. 2, 2018, US20190069604.

U.S. Appl. No. 16/181,316, filed Nov. 5, 2018, US20190069605.

U.S. Appl. No. 16/193,994, filed Nov. 16, 2018, US20190082741.

U.S. Appl. No. 16/193,943, filed Nov. 16, 2018, US20190082740.

"New Tank E-Cigarette:innokin 510T." From China Manufacturer, Manufactory, Factory and Supplier on ECVV.com, Nov. 15, 2011, www.ecvv.com/product/3118191.html.

Chinabuye. "Innokin ITaste VV Tank Starter Kit Electronic Cigarette with Clearomizer." YouTube, YouTube, Jul. 23, 2013, www.youtube.com/watch?v=mz414d8MU20.

Cloud pen vaporizer unboxing review by vaporizer blog // VaporizerBlog.com, https://www.youtube.com/watch?v=jxHMkXoWKNg.

Glory Vapes. "Glory Vapes TV: Kanger S1 Cubica Series Starter Kit Unboxing." YouTube, YouTube, Aug. 8, 2013, www.youtube.com/watch?v=NQjvJ6YhdbA.

Joye eGo-Tank System XXL 1000mAh Starter Kit, https://www.myvaporstore.com/eGo-Tank-System-XXL-1000mAh-Starter-Kit-p/ego-t-xxlkit.htm.

Uptoyou Fromeme. "Elips Ego SOLE Electronic Cigarette Kit Patent Elipse Flat Upgrade F6 Section with Atomizer CE4." YouTube, YouTube, Sep. 12, 2013, www.youtube.com/watch?v=cnPcqDzFm0Q.

Vaporizers Reviewed. "AtmosRX Optimus 510 Vaporizer Review." YouTube, YouTube, Oct. 10, 2013, www.youtube.com/watch?v=wsyQncG8FB8.

Vaporizers Reviewed. "MicroG Pen Vaporizer Review." YouTube, YouTube, Nov. 6, 2013, www.youtube.com/watch?v=pLhtL8vosrs.

* cited by examiner

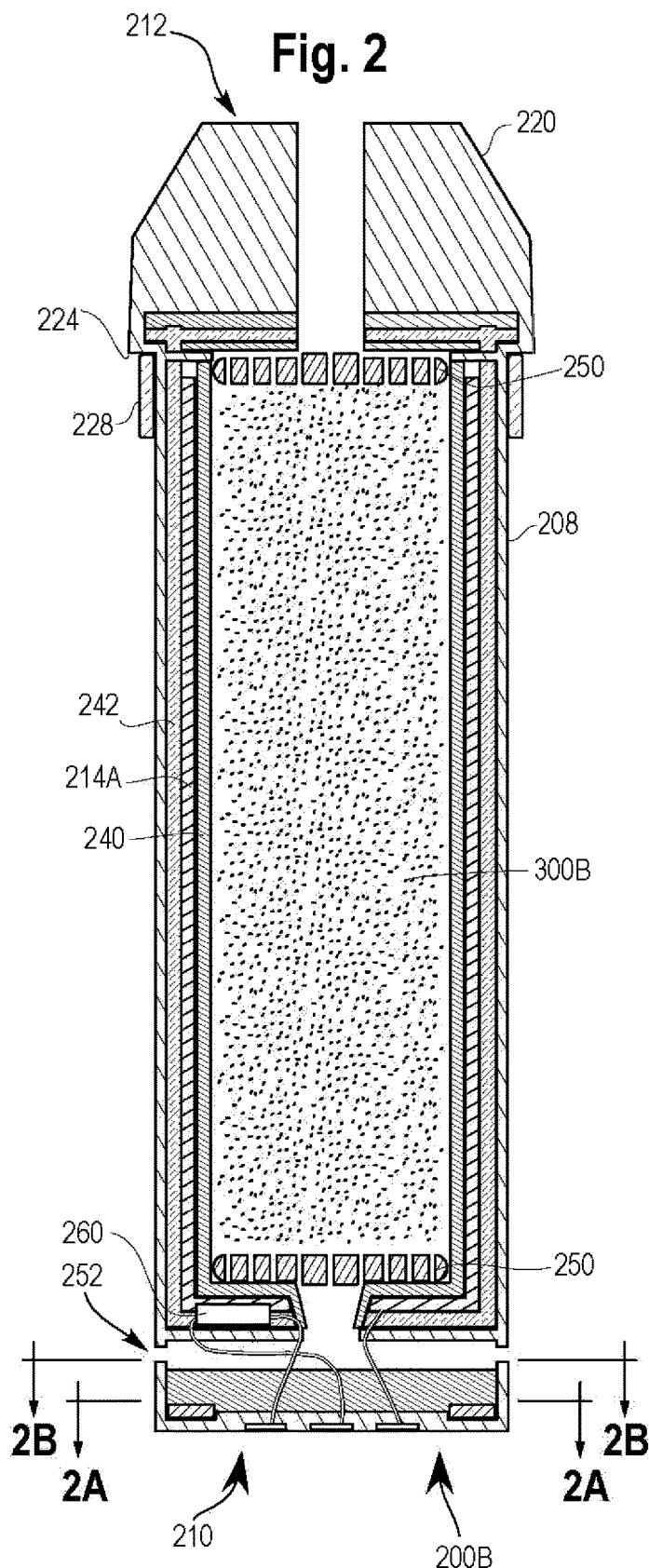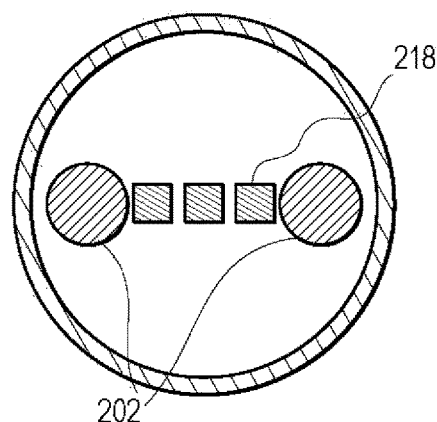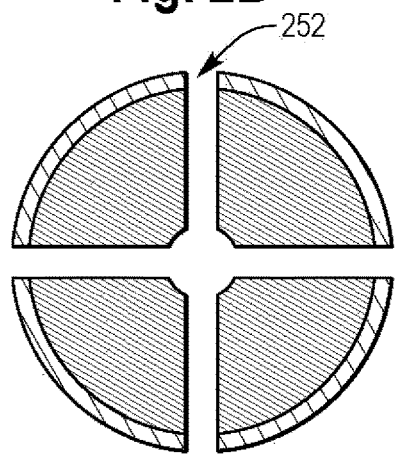

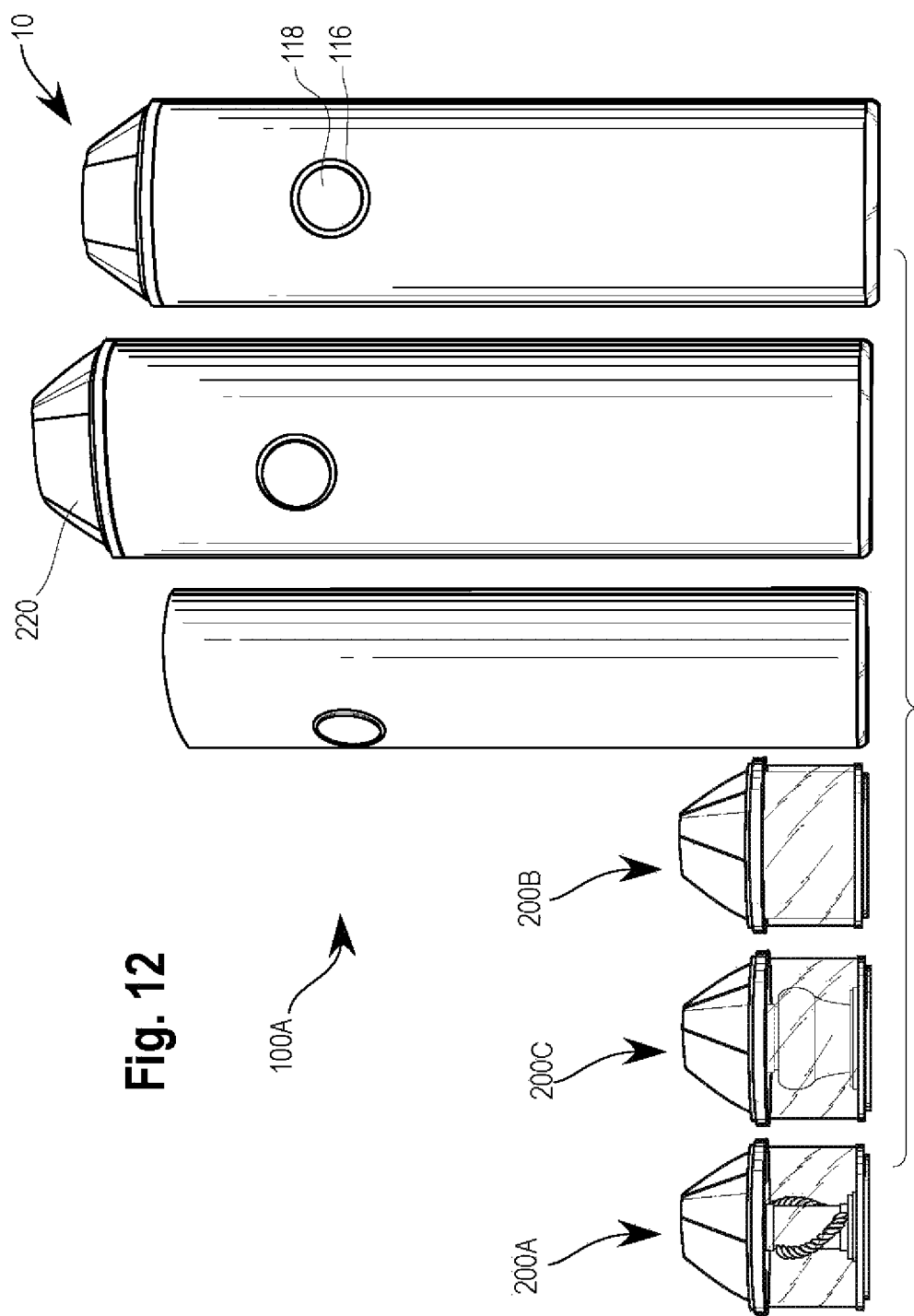

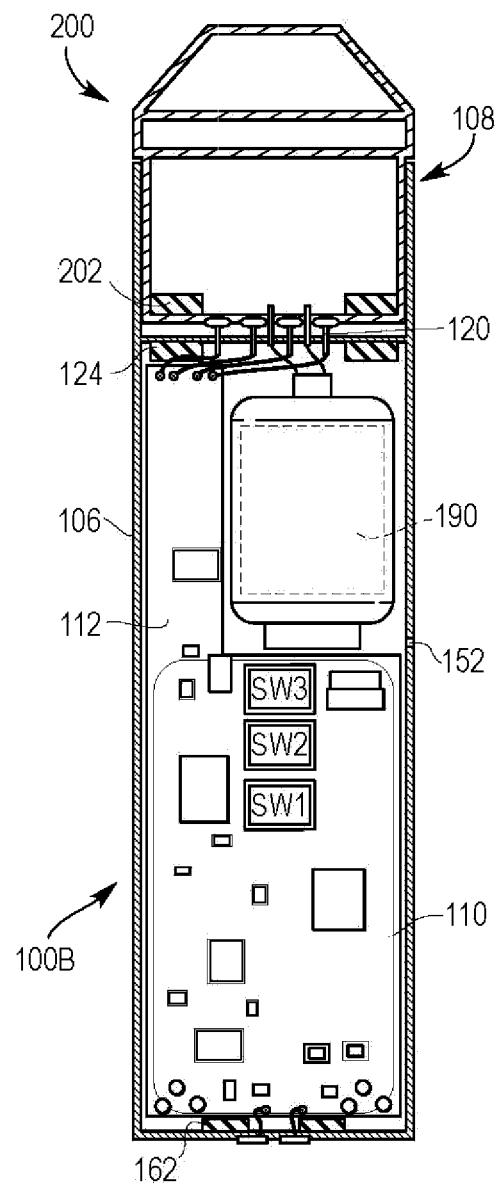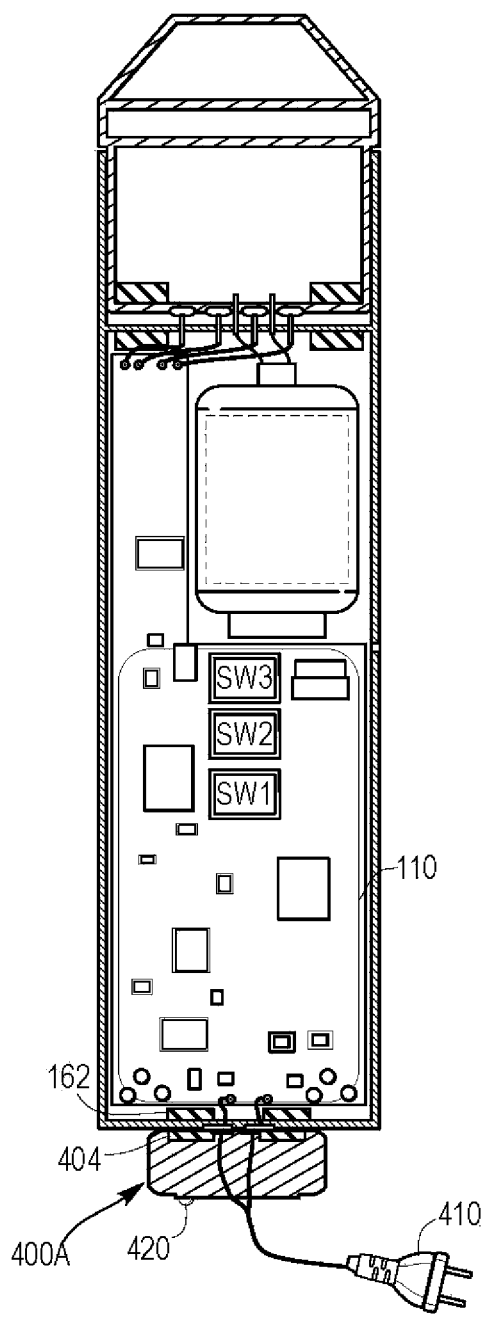

VAPORIZER, CHARGER AND METHODS OF USE

CROSS REFERENCE TO RELATED APPLICATIONS

This application is a continuation of U.S. application Ser. No. 14/196,729, filed Mar. 4, 2014 which claims the benefit of U.S. Provisional Application Nos. 61/903,344 filed Nov. 12, 2013, and 61/937,851, filed Feb. 10, 2014, the disclosures of which are hereby incorporated herein by reference in their entireties.

FIELD OF THE INVENTION

This invention relates to the field of vaporizers, which may also be referred to as electronic cigarettes.

BACKGROUND

Electronic cigarettes have recently emerged as a new product for providing nicotine through a smokeless inhalation process. Typically, implementations consist of a power supply (typically a battery) and an atomizing device. In reusable electronic cigarettes the two items are separated into a battery and a cartomizer, to allow the disposal and replacement of a nicotine containing fluid cartomizer while preserving the more costly battery and associated circuitry (microcontroller, switch, indicating LED, etc.) for additional use. In disposable electronic cigarettes, the two items are combined to integrate the functions into one unit that is discarded after either the battery energy or the nicotine containing liquid is exhausted.

The electronic cigarette liquid used to vaporize ingredients such as nicotine is generally a solution of propylene glycol (PG), vegetable glycerin (VG), or polyethylene glycol 400 (PEG400), as well as their mixtures to which a flavor and/or nicotine has been added. The solution is often sold in a bottle (for refilling by the user) or in disposable cartridges or cartomizers. Many different flavors are incorporated into these liquids, including those that resemble the taste of regular tobacco, menthol, vanilla, coffee, cola and/or various fruits. Various nicotine concentrations are also available, and nicotine-free solutions are also common.

BRIEF SUMMARY

One embodiment of a vaporizer, in accordance with the disclosure, may include a shell having a battery segment and a cartomizer receiving segment, the cartomizer receiving segment may define a chamber having an insertion end distal to the battery segment of said shell and a base end proximate to the battery segment, the chamber dimensioned to receive a cartomizer inserted into the chamber at the insertion end of the chamber. The vaporizer may also include a battery housed within the battery segment. The vaporizer may further include electrical contacts provided between the base end of the chamber and the battery portion, the electrical contacts including a positive contact and a negative contact insulated from the positive contact. Electronic circuitry may be housed within the battery segment of said shell and operable to direct an electrical current between the battery and the electrical contacts. Additionally, a chamber magnet may be provided in or proximate to the chamber, the chamber magnet operable to secure a cartomizer received within the chamber, wherein the cartomizer includes either a metallic surface or a cartomizer magnet having a polarity opposite to that of the chamber magnet. The electrical contacts and battery may each be in electrical connection with said electronic circuitry. The cartomizer may be securable within the chamber as a cartomizer surface and a magnetically attracted chamber surface are placed adjacent to one another.

In another embodiment of a vaporizer, in accordance with the disclosure, the vaporizer may include a shell having a battery segment and a cartomizer receiving segment, the cartomizer receiving segment defining a chamber having an insertion end distal from the battery segment and a base end proximate to the battery segment. The vaporizer may further include a cartomizer insertable into the chamber at the insertion end, and the cartomizer may include a cartomizer body dimensioned to hold a vaporizable substance, a heating element provided within or proximate to the cartomizer body operable to heat the vaporizable substance, cartomizer electrical contacts provided on the exterior of the cartomizer, cartomizer electrical circuitry operable to direct an electronic current between the cartomizer electrical contacts and the heating element, and a mouthpiece in fluid communication with the cartomizer body, the mouthpiece extending from the insertion end of the chamber when the cartomizer is inserted in the chamber. The heating element may be activated by the current and is operable to heat the vaporizable substance to a vaporization temperature. A battery may be housed within the battery segment. The vaporizer may also include battery electrical contacts provided between the base end of the chamber and the battery segment, the battery electrical contacts positioned to contact the cartomizer electrical contacts when the cartomizer is inserted in the chamber. Additionally, the vaporizer may include battery electrical circuitry housed within the battery segment and operable to direct an electrical current between the battery, the battery electrical contacts, the cartomizer electrical contacts, the heating element, and the inserted cartomizer.

BRIEF DESCRIPTION OF THE FIGURES

FIG. 2 illustrates a front view of an embodiment of a cartomizer in accordance with the disclosure that may be inserted into the cartomizer chamber of the battery portion of FIG. 1, the outer shell of the first embodiment battery portion shown transparently so as to illustrate the inner components of the electronic cigarette.

FIG. 2A illustrates a lateral cross sectional view of the cartomizer of FIG. 2 illustrating the end of the cartomizer at the inserted end.

FIG. 2B illustrates a lateral cross sectional view of the cartomizer of FIG. 2 illustrating the air hole structure.

FIG. 12 illustrates embodiments of electronic cigarettes comprising the second battery portion of FIGS. 8-9 and the cartomizers of FIGS. 8-10.

FIG. 13 illustrates a front view of an embodiment of an electronic cigarette in accordance with the disclosure, with the outer shell of the embodiment of the battery portion shown transparently so as to illustrate the inner components of the electronic cigarette.

FIG. 14 illustrates a front view of the electronic cigarette of FIG. 13 with a charger attached.

DETAILED DESCRIPTION

Figure 1:
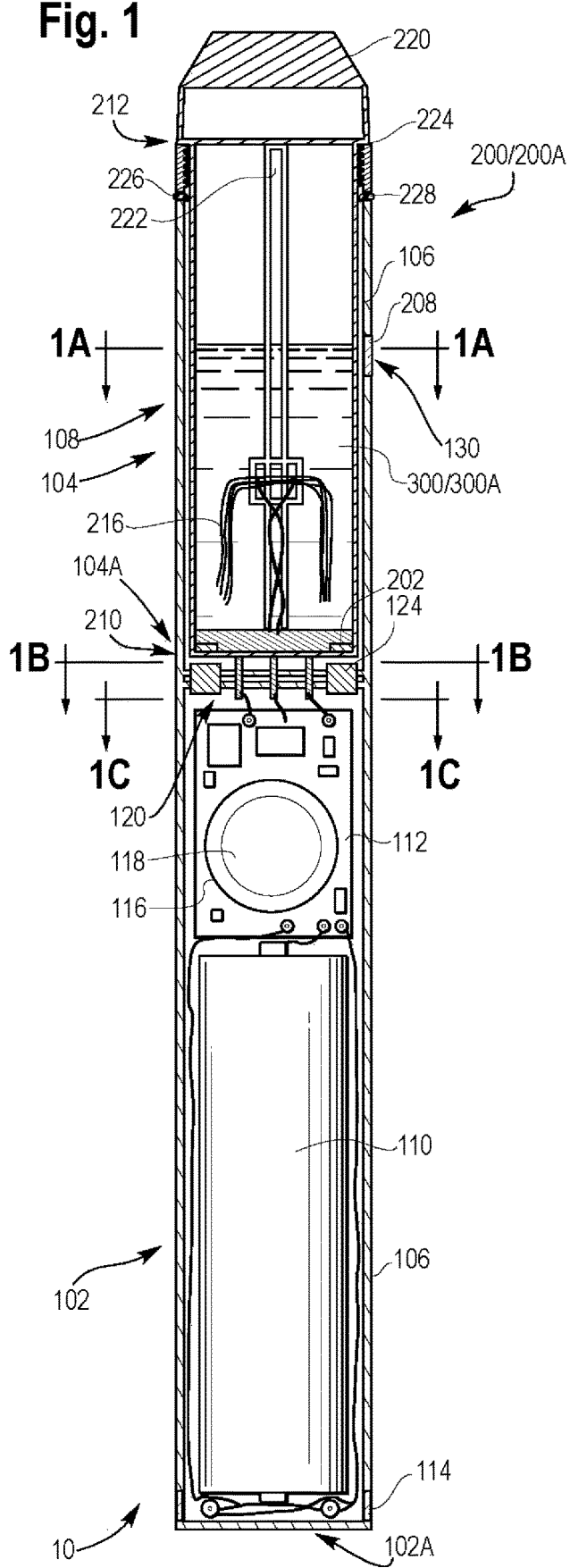
FIG. 1 illustrates a front view of an embodiment of an electronic cigarette of the disclosure comprising a first embodiment of a battery portion with an embodiment of a cartomizer for use with a vaporizable liquid inserted into a cartomizer chamber of the first embodiment battery portion, the outer shell of the first embodiment battery portion shown transparently so as to illustrate the inner components of the electronic cigarette.

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings are not to scale and in certain instances details have been omitted, which are not necessary for an understanding of the present invention, such as conventional details of fabrication and assembly.

One embodiment of a vaporizer, in accordance with the disclosure, may include a shell having a battery segment and a cartomizer receiving segment, the cartomizer receiving segment may define a chamber having an insertion end distal to the battery segment of said shell and a base end proximate to the battery segment, the chamber dimensioned to receive a cartomizer inserted into the chamber at the insertion end of the chamber. The vaporizer may also include a battery housed within the battery segment. The vaporizer may further include electrical contacts provided between the base end of the chamber and the battery portion, the electrical contacts including a positive contact and a negative contact insulated from the positive contact. Electronic circuitry may be housed within the battery segment of said shell and operable to direct an electrical current between the battery and the electrical contacts. Additionally, a chamber magnet may be provided in or proximate to the chamber, the chamber magnet operable to secure a cartomizer received within the chamber, wherein the cartomizer includes either a metallic surface or a cartomizer magnet having a polarity opposite to that of the chamber magnet. The electrical contacts and battery may each be in electrical connection with said electronic circuitry. The cartomizer may be securable within the chamber as a cartomizer surface and a magnetically attracted chamber surface are placed adjacent to one another.

In some embodiments, the chamber magnet may be provided proximate to the base end of the chamber, the chamber magnet insulated from the electrical contacts. The vaporizer may further include an additional chamber magnet provided proximate to the base end of the chamber, the additional chamber magnet insulated from the electrical contacts and the chamber magnet, the additional chamber magnet having a polarity opposite to that of the chamber magnet. The electronic circuitry may include a printed circuit board.

Additional embodiments of the vaporizer may include an activation button provided on the exterior of the shell in electrical communication with the electronic circuitry, the electrical contacts and the battery, wherein manipulation of the activation button by a user of the vaporizer operates to control the current from the battery to the electronic contacts; a printed circuit board; and an indicator ring surrounding at least a portion of the activation button, the indicator ring in electrical communication with the electronic circuitry, the electrical contacts and the battery, said indicator ring illuminable to indicate a state of the vaporizer, the indicator ring controllable by the printed circuit board, and the printed circuit board may be in electrical communication with the electrical contacts, the battery, the activation button and the indicator ring. The vaporizer may also include a display screen provided on the exterior of the shell, said display screen in electrical communication with said printed circuit board and battery, the display screen controlled by the printed circuit board and operable to display a message. At least one of the electrical contacts may be a spring-loaded pin extending into a portion of the chamber and retractable when pressed by the cartomizer when inserted into the chamber. The shell may include a window provided at the cartomizer receiving segment so that a portion of the chamber is visible from outside the shell.

In another embodiment of a vaporizer, in accordance with the disclosure, the vaporizer may include a shell having a battery segment and a cartomizer receiving segment, the cartomizer receiving segment defining a chamber having an insertion end distal from the battery segment and a base end proximate to the battery segment. The vaporizer may further include a cartomizer insertable into the chamber at the insertion end, and the cartomizer may include a cartomizer body dimensioned to hold a vaporizable substance, a heating element provided within or proximate to the cartomizer body operable to heat the vaporizable substance, cartomizer electrical contacts provided on the exterior of the cartomizer, cartomizer electrical circuitry operable to direct an electronic current between the cartomizer electrical contacts and the heating element, and a mouthpiece in fluid communication with the cartomizer body, the mouthpiece extending from the insertion end of the chamber when the cartomizer is inserted in the chamber. The heating element may be activated by the current and is operable to heat the vaporizable substance to a vaporization temperature. A battery may be housed within the battery segment. The vaporizer may also include battery electrical contacts provided between the base end of the chamber and the battery segment, the battery electrical contacts positioned to contact the cartomizer electrical contacts when the cartomizer is inserted in the chamber. Additionally, the vaporizer may include battery electrical circuitry housed within the battery segment and operable to direct an electrical current between the battery, the battery electrical contacts, the cartomizer electrical contacts, the heating element, and the inserted cartomizer.

In embodiments of the disclosure, the vaporizable substance may be a fluid, the heating element may include a wicking element for absorbing the fluid, and at least a portion of the cartomizer body may be composed of a translucent material. The cartomizer may further include a container provided within the cartomizer body and dimensioned to hold the vaporizable substance, wherein the heating element is provided exterior to at least a portion of the container and is operable to heat the container thereby heating the vaporizable substance to the vaporization temperature. The heating element may include conductive material intertwined with non-conductive material, and the conductive material may be in electrical communication with the cartomizer electronic circuitry. The vaporizer may further include a printed circuit board housed in the battery segment and in electrical communication with the battery electrical circuitry, and the cartomizer may further include a sensor in electrical communication with the cartomizer electrical circuitry, and the printed circuit board is operable to process environment information received from the sensor when the cartomizer is inserted into the chamber. The mouthpiece may be detachably connected to the cartomizer body. The cartomizer may further include a basin for holding the vaporizable substance, and the heating element may be provided proximate to the basin in order to heat the basin.

With reference now to FIGS. 1 and 2, an embodiment of an electronic cigarette 10 is provided in accordance with the disclosure. Electronic cigarette 10 may include a battery portion connectable with a vaporization unit or cartomizer 200 for holding a vaporizable substance 300. The battery portion may include a battery housing segment 102 provided proximate to the first end 102A of the battery portion, and a second cartomizer receiving segment 104 provided proximate a second end 104A of the battery portion. The battery portion may include an outer shell 106 for covering or protecting one or more of the components of battery portion 100 as may be internally provided as described herein. Outer shell 106 may be substantially constructed from metal, plastic, or any other known or to be developed material suitable for protecting internal components of electronic cigarette 10, including the electrical components described herein. Battery housing segment 102 and cartomizer receiving segment 104 may commonly share outer shell 106. A cartomizer chamber 108 may be provided within at least a portion of cartomizer receiving segment 104. A cartomizer 200 may be insertable into the cartomizer chamber 108 in accordance with embodiments of the disclosure. Shell 106 may cover cartomizer chamber 108 thereby protecting an inserted or received cartomizer 200.

Electrical components for operating electronic cigarette 10 may be provided within battery housing segment 102. A battery 110 may be provided in order to provide electrical power as may be required by various features of the electronic cigarette 10. In some embodiments, battery 110 may be disposable, such as an AA or AAA cell battery, while in other embodiments, battery 110 may be of a rechargeable type, for example a 13450 lithium ion battery, an 18650 2600 mAh lithium ion cell, or flat lithium ion 903180 cell rated at 2300 mAh. Multiple batteries 110 may be used in series to generate higher voltages capable of shortening times to achieve vaporization temperatures in the cartomizer 200. A printed circuit board (PCB) 112 may also be provided for controlling one or more functions of electronic cigarette 10. PCB 112 may be electrically connected to battery 110 through circuitry in order to direct current flow as required in accordance with the disclosure. PCB 112 may include one or more integrated circuit chips as well as a micro control unit. A boost chip may also be provided in order to amplify voltage with at least portion of circuitry, as may be required in order to accomplish various functions described herein. PCB 112 may include a light emitting diode (LED), a microcontroller, a plurality of capacitors, a plurality of transistors, and a plurality of resistors or any combination thereof. An accelerometer for sensing gravity shifts of electronic cigarette 10 may be further provided. The accelerometer may be operable to detect tilting or changes in orientation of battery portion 100, and PCB 112 may be accordingly operable to react to a shift in orientation detected by the accelerometer. For instance, electronic cigarette 10 including an accelerometer may be activated by shaking or inverting electronic cigarette 10. Any known or to be discovered circuitry or arrangement of the components of PCB 112 are contemplated within the disclosure in order to achieve the desired functions of electronic cigarette 10 as described herein.

A variety of indicator lights forming one or more illuminative indicators may be provided in embodiments of the disclosure. One such indicator may be a battery end indicator 114 provided as a ring extending about at least a portion of shell 106 at or proximate to first end 102A. In one such embodiment, battery end indicator 114 may be provided at or proximate to first end 102A and includes one or more LED lights having one or more colors. Each color may, for instance, indicate a status of electronic cigarette 10. The status may be associated with the power remaining of battery 110, an activation state of electronic cigarette 10, the heating level of an inserted cartomizer 200, or any other status which may be desirable to communicate to a user of electronic cigarette 10 through a light color. For instance, when electronic cigarette 10 is activated such that a user is either actively inhaling cigarette 10, as described in accordance with disclosure, or cigarette 10 is in a state such that the user could inhale, indicator 114 may be red or reddish. In such an embodiment, battery end indicator 114 could extend about at least a portion of the first end 102A such that when indicator 114 emanates a red or reddish color a user may associate the red color at or proximate to first end 102A with the red glow of a lit cigarette. In another embodiment, an indicator ring may be provided to illuminate one or more colors associated with the charge or power state of battery 110. For instance, battery end indicator 114 may illuminate green or blue when the battery is operating with a sufficient charge, and yellow or red when the battery is operating with a low charge such that the user should consider charging battery 110, in accordance with the disclosure. A ring indicator 116 may be provided on or proximate to an activation button 118, which may function to activate cigarette 10 as described herein in accordance with the disclosure. While activation button 118 may be provided on the surface of outer shell 106, and ring indicator 116 may substantially circumference button 118. Ring indicator 116 may include one or more LED lights having one or more colors to indicate various statuses of electronic cigarette 10. Status changes of electronic cigarette 10, such as insertion of cartomizer 200, activation of electronic cigarette 10 by pressing button 118, or deactivation of electronic cigarette 10 by pressing button 118 an additional time may each result in a different associated and predetermined color. The activation of the appropriate LED light or lights may be controlled by PCB 112. In embodiments where button 118 is coplanar or aligned with the surface of outer shell 106, as described herein, ring indicator 116 may also be coplanar or aligned with button 118 and the surface of outer shell 106. Another indicator light may be provided at or proximate to cartomizer end 104A. In one embodiment, in order to transmit a lighting effect from the battery segment 102, where battery 110 and PCB 112 may be housed, to the cartomizer end 104A, one or more LED lights may be provided in the cartomizer receiving segment 104 at or proximate to the battery segment 102. One or more clear tubes or optic fibers may be also be provided within or just below the surface of outer shell 106, with the tubes or fibers terminating at or proximate to the cartomizer end 104A. The resulting effect is an attractive, illuminative effect where the LED lights provided in the cartomizer segment are projected into and transmitted along the fibers. PCB 112 could potentially alternate or change the LED light colors projected into the fibers. The color alternation could be periodic, creating a steady change of colors, or the color alteration could be responsive to a status change of the electronic cigarette 10.

In order to provide an electrical connection between PCB 112 and an inserted cartomizer 200, an electrical connector 120 may be provided and may include a plurality of pogo pins 120. Pogo pins are devices used to establish connections between two circuits, and each may take the form of a cylinder containing one or more spring-loaded pins 122, each retractable upon compression, for instance by cartomizer 200 when it is inserted in cartomizer chamber 108. In one such embodiment, three pogo pins 122 may be provided, one for establishing positive current connection, one for establishing a negative current connection, and one for establishing a ground current connection. Each pogo pin 122 may be connected to PCB 112, which may control current outputted to pogo pins 122. For instance, PCB 112 may operate to vary or intermittently activate current flow to connector 120, the variation thereby regulating the activation of a heating element in a connected cartomizer. When cartomizer 200 is not received in cartomizer chamber 108, a head portion of each pogo pin may extend into cartomizer chamber 108. When cartomizer 200 is received in cartomizer chamber 108, the pins 122 are contacted and at least partially compressed into battery portion 102. Pins 122 may be contacted or pressed against electrical receivers provided on cartomizer 200 as described herein, thereby establishing an electrical connection between PCB 112 and cartomizer 200. Additional pins 122 are contemplated in embodiments of the disclosure, such as a fourth pin for providing an electrical connection to another element, such as the LED lights described above or a temperature sensor 260 described herein and illustrated in FIG. 2.

An additional embodiment of connector 120 may operate to identify information from an inserted cartomizer 200 based on voltage drop over one or more pins 122. For instance, connector 120 may include a controlling pin 122 from which connected PCB 112 may detect variations in voltage drop across the pin when connected to various types of cartomizers 200. Circuitry provided within a first type of cartomizer 200 may effectuate a first voltage drop over a controlling pin 122, while circuitry provided within a second type of cartomizer 200 may effectuate a second voltage drop over controlling pin 122 when cartomizer 200 is inserted in chamber 108. If PCB 112 detects a first voltage drop, the cartomizer 200 is identified as a first type of cartomizer, whereas if PCB 112 detects a second voltage drop, the cartomizer is identified as second type of cartomizer. A first cartomizer type may hold a first type of vaporizable substance 300, while a second cartomizer type may hold a second type of vaporizable substance 300. In one embodiment, connector 120 includes three pins 122: a positive pin, a ground pin, and a controlling pin. A controlling pin may also serve a dual function in that communication between a sensor 260 may also occur through a controlling pin 122. Other known or to be developed devices or connectors are contemplated within the disclosure for establishing an electrical current between PCB 112 and cartomizer 200.

Figure 1A:
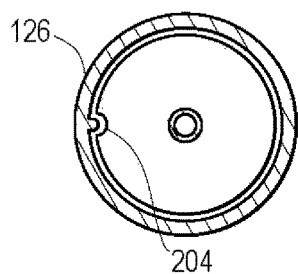
FIG. 1A illustrates a lateral cross sectional view of the electronic cigarette of FIG. 1 illustrating an electrical connector and magnets.
Figure 1B:
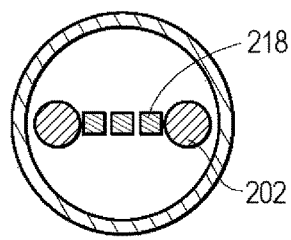
FIG. 1B illustrates a lateral cross sectional view of the electronic cigarette of FIG. 1 illustrating the end of the inserted cartomizer.

Various features may be further provided in embodiments of electronic cigarette 10 in order to secure and align cartomizer 200 within cartomizer chamber 108. For instance, at least one magnet 124 may be provided in or proximate to chamber 108. A magnet 202 of opposing polarity to magnet 124 may be placed on a surface of cartomizer 200 so as to secure cartomizer 200 within chamber 108 when magnets 124, 202 (see FIGS. 1A, 1B) contact each other. It should be understand and appreciated that, in some embodiments, battery portion magnet(s) 124 may attach to cartomizer metallic surface(s) 202 and, conversely, cartomizer magnet(s) 202 may attach to battery portion metallic surface(s) 124, thereby establishing a magnetic connection between battery portion 100 and cartomizer 200. Other known or to be discovered means of securing cartomizer 200 in cartomizer chamber 108 are contemplated within the disclosure, including but not limited to, snap fit connectors, friction fit, threaded insertion of cartomizer 200 into chamber 108, a suction fit using pressurized means or any other suitable method of securing known or to be developed in the art.

Figure 1C:
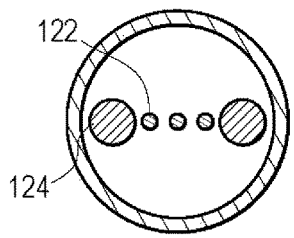
FIG. 1C illustrates a lateral cross sectional view of the electronic cigarette of FIG. 1 illustrating the cartomizer chamber.

One or more alignment features or mechanism may be included in order to ensure proper placement of cartomizer 200 in cartomizer chamber 108. In one embodiment, two magnets 124 may be provided proximate to connector 120 (see FIG. 1A), each magnet 124 having an opposed polarity. In this embodiment, two cartomizer magnets 202 (see FIG. 1B) may be provided of opposing polarity at an insertion end 210 of cartomizer 200. Because of the opposing polarities of magnets 124/202, the cartomizer 200 may only be inserted and secured in one direction or orientation, thereby facilitating alignment of cartomizer 200 within chamber 108. An alignment protrusion or peg 126 (see FIG. 1C) may be provided on a portion of an interior surface of chamber 108, and an alignment slit or slot 204 may be provided on a portion of cartomizer 200. Alignment protrusion 126 may be dimensioned to fit or slid along slit 204 so that cartomizer 200 may only be inserted in a particular, proper orientation. In another embodiment, a slit, crevice, or cutout may be provided on a portion of shell 106, with a matching protrusion provided on a portion cartomizer 200. For instance, a cutout may be provided on an upper rim of shell 106 at cartomizer receiving segment 104, while a matching protrusion may be provided on a portion of cartomizer 200 proximate to insertion end 210, with battery portion cutout engageable with the cartomizer protrusion when the cartomizer is properly aligned so as to ensure proper orientation of cartomizer 200 within chamber 108. Ensuring cartomizer 200 is properly oriented within chamber 108 in turn ensures proper contacting of cartomizer 200 with connector 120, and therefore proper functioning of electronic cigarette 10.

One or more windows 130 may be provided in outer shell 106 (see FIG. 1). Windows 130 may be made of a translucent material, such as glass or substantially clear plastic, in order to view internal components of battery portion 100. Window 130 may also be a slit cut into shell 106. For instance, in one embodiment, window 130 may be provided on or proximate to cartomizer receiving segment 104 and, more particularly, cartomizer chamber 108 so as to permit a user of electronic cigarette 10 to view the cartomizer 200 when it is inserted into cartomizer chamber 108.

One embodiment of cartomizer 200 for holding vaporizable material 300 is cartomizer 200A for holding a vaporizable fluid 300A, an embodiment of which is illustrated in FIG. 1. Vaporizable fluid 300A may be, for example, any known or to be developed fluid useful to vaporize, for inhalation nicotine, flavor or other desired ingredients in an electronic cigarette, such fluids include propylene glycol (PG), vegetable glycerin (VG), or polyethylene glycol 400 (PEG400), as well as their mixtures to which a flavor and/or nicotine has been added. Cartomizer 200A may be substantially elongate and insertable into chamber 108. Chamber 108 is defined by outer shell 106 and electrical connector 120. An insertion end 210 of cartomizer 200A, defined opposite of a mouthpiece end 212, may be inserted into the chamber first and may ultimately contact or be positioned proximate to connector 120 of battery portion 100. Cartomizer 200A may include a body 208 for holding fluid 300A. At least a portion of body 208 may be composed of translucent or substantially translucent material, such as glass or plastic, so that a user may see fluid 300A held within. The portion of body 208 composed of translucent material may be alignable with window 130 and may be proximate to LED lights or fiber optics so as to illuminate cartomizer 200A as it is inserted into chamber 108. The illumination may occur automatically upon insertion, or may be programmed to illuminate upon activation or manipulation of a switch, such as button 118.

In order to vaporize fluid 300A, a heating element 214 and a wicking element 216 may be provided within cartomizer body 208. An electrical current may be transmitted to heating element 214 through circuitry in electrical communication with electrical contacts, which contact pins 122 (see FIG. 1A) when cartomizer 200A is inserted into chamber 108. Once fluid 300A is heated to an optimal vaporizing temperature, the user may inhale the vaporized fluid 300A through a mouthpiece 220 provided on body 208 at or proximate to mouthpiece end 212. The vaporized fluid may travel through an inhalation tube 222 in fluid connection with heating element 214 and wick 216. Inhalation tube 222 may also be in fluid communication with one or more holes or ducts provided, for instance, in sides of outer shell 106 in order to permit air flow through cartomizer body 208. The electrical current transmitted to heating element 214 may be controlled by PCB 112 through connector 120 when cartomizer 200A is inserted into chamber 108. The electronic cigarette 10 may be manually controlled, as a user may press button 118 to initiate a charge to heating element 214, which in turn may heat fluid 300A to a vaporized temperature which a user may inhale through mouthpiece 220. An automatically heating version of electronic cigarette 10 is also contemplated with disclosure, where a pressure switch integrated with connector 120 may activate current flow from PCB to heating element 214 rather than by manual activation from switch 118.

So that a user may refill fluid 300A held in body 208, mouthpiece 220 may be removable from body 208. Mouthpiece 220 may include a screw thread 224 so that mouthpiece 220 may be threadably engaged with mouthpiece end 212 of body 208 or, alternatively, may be press fit onto or into mouthpiece end 212 of body 208. A bushing 226, which may be a ring formed from plastic, rubber, or any other suitable material, may be provided to help stabilize and retain cartomizer 200 tightly fit in chamber 108. Additionally, a colored ring or logo 228 may be provided about a portion of cartomizer body 208 in order to identify the type or cartomizer being used.

With reference now to FIGS. 2, 2A and 2B, an additional embodiment of cartomizer 200B is provided for holding a dry vaporizable material 300B, such as dry tobacco. A container 240 may be provided within cartomizer body 208. Container 240 may be made from a material having a high thermal conductivity, such as metal, in order to transmit heat from a heating element 214A provided about at least a portion of container 240. In that at least a portion of heating element 214A may be provided about at least a portion of container 240, the material 300B provided within container 240 may be heated from multiple sides, similar to an oven, as opposed to from a single concentrated heat source. As an electrical current is transmitted to heating element 214A, the interior of container 240 may be heated to a desired vaporizing temperature. Heating element 214A may be substantially comprised of a non-conductive material, such as a polyimide flex harness material, with a conductive material, such a copper or other metal wiring shaped into a wire or flat ribbon, dispersed throughout the non-conductive material. The conductive material may be intertwined or wound throughout the non-conductive material in order to increase the heated surface area as well as to increase the impedance of the conductive material, which may then be electrically connected to PCB 112 through connector 120 when cartomizer 200B (See FIG. 2) is inserted in cartomizer chamber 108 (See FIG. 1). The impedance value of the conductive material may be 2-3 ohms in some embodiments, and in one embodiment a maximum of 1 ohm. In some embodiments, heating element 214A may be provided around the majority of cartomizer body 208, and in some embodiments heating element 214A may be provided proximate to only a portion of cartomizer body 208. For instance, heating element 214A may be provided only proximate to insertion end 210, in order to provide a greater portion of heating through convection rather than through conduction. In some embodiment, heating element 214A may be provided about all or the majority of body 208, and PCB 112 may be operable in order to vary the amount of heating provided through convection rather than conduction. For instance, only the portion of heating element 214A proximate to insertion end 210 may be activated in order to heat vaporizable substance 300B through convection, or all or nearly all portions of heating element 214A may be activated in order to increase the conduction heating of substance 300B. PCB 112 may operate to switch between a conduction heating and a convection heating.

An insulating material 242 may be further provided within body 208 in order to control or regulate the heat distribution. Insulating material 242 may be provided around at least a portion of the exterior of heating element 214A in order to insulate body 208 from excess heat temperature, which may transmit to outer shell 106 (See FIG. 1). Insulating material 242 may also be provided between heating element 214A and container 240 so as to regulate or control heat transmitted to container 240.

One or more screens 250 may be provided within body 208 in order to contain dry material 300B within container 240, as well as to filter circulated air. Air may be circulated by providing one or more holes 252 in the cartomizer body 208. In one embodiment, holes 252 form a "t" shape (See FIG. 2B) from which the center of the "t" is substantially aligned with a hole leading to container 240. Holes 252 may be capable of alignment with one or more holes on the outer shell 106 of battery portion 100 so that air from the environment may pass through holes 252 and into container 240 where material 300B is provided. Holes 252 may be provided proximate to the inserted end 210. Screens 250 may be provided either at or proximate to inserted end 210, mouthpiece end 212, or both. In some embodiments, container 240 is removable from the rest of cartomizer body 208. Mouthpiece 220 may be removable or detachable, for instance through a screw thread, so as to permit access to container 240. An upper screen 250 may be attached or manufactured integrally with mouthpiece 220 so as to be removed with mouthpiece 220.

A sensor 260 may be included in some embodiments of cartomizer 200. Sensor 260 may operate to sense vaporizing temperature, and may be electronically communicative with PCB 112 so as to provide sensory information to PCB 112, which may be consequently transmitted to one of the LED indicators provided in electronic cigarette 10 as described in accordance with the disclosure. For instance, indicator 118 (See FIG. 1) may illuminate a certain color when sensor 260 has detected that vaporization temperature in container 240 has been reached and the user may proceed to inhale vaporized material 300. PCB 112 may also including safety protocols for automatic shutoff in the event that sensor 260 records a temperature above a preset vaporization temperature range, which may indicate material 300 (including, for example, 300A, 300B, 300C) is actively burning or about to burn. Thus, sensor 260 may operate as a thermistor. A vaporization range for many materials 300 may be between about 190 degrees Celsius and about 240 degrees Celsius, and in some embodiments the vaporization temperature may be at about 230 degrees Celsius. In this vaporization temperature range, active ingredients of the vaporization material 300 may begin to vaporize without actively burning, which may occur at about 400 degrees Celsius or higher for some materials. PCB 112 may operate to control the vaporization temperature, for instance regulating a maximum vaporization temperature or controlling the vaporization actual temperature. In one embodiment, PCB 112 may control or regulate vaporization temperature within 10 degree Celsius, and in another embodiment PCB 112 may more finely control or regulate vaporization temperature within 1 degree Celsius, based on a selected or desired vaporization temperature as inputted by a user of electronic cigarette 10. It should be understood and appreciated that communication between sensor 260 and PCB 112 may be bidirectional so that sensor 260 may operate to control at least portions of vaporizer functions or to transmit information to PCB 112 and additionally receive information from PCB 112, which operates to control electronic cigarette 10.

Figure 3:
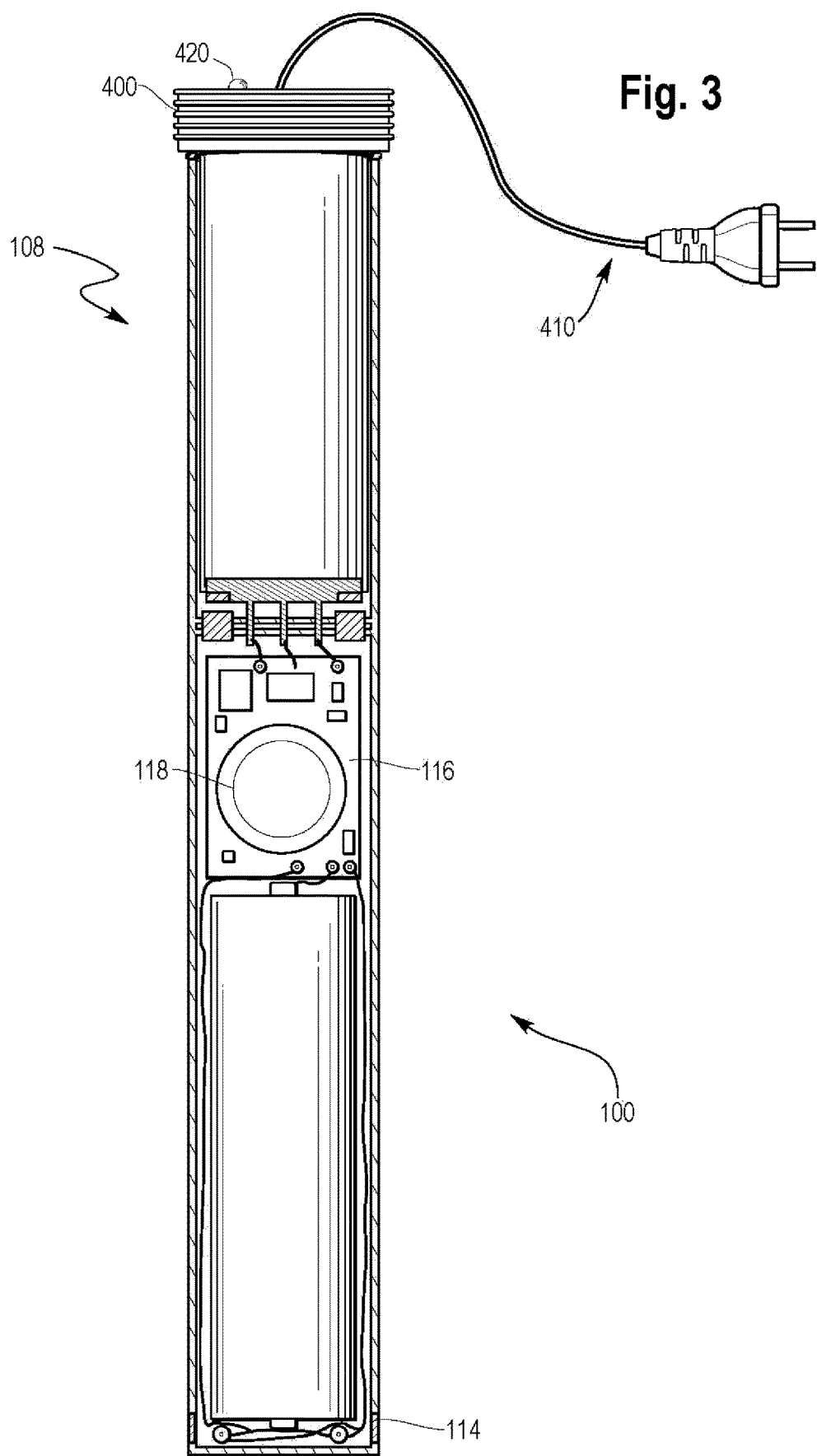
FIG. 3 illustrates a front view of an embodiment of the battery portion of FIG. 1 with an embodiment of a charger, in accordance with the disclosure, inserted into the cartomizer chamber, with the outer shell of the first embodiment battery portion shown transparently so as to illustrate the inner components of the electronic cigarette.
Figure 4:
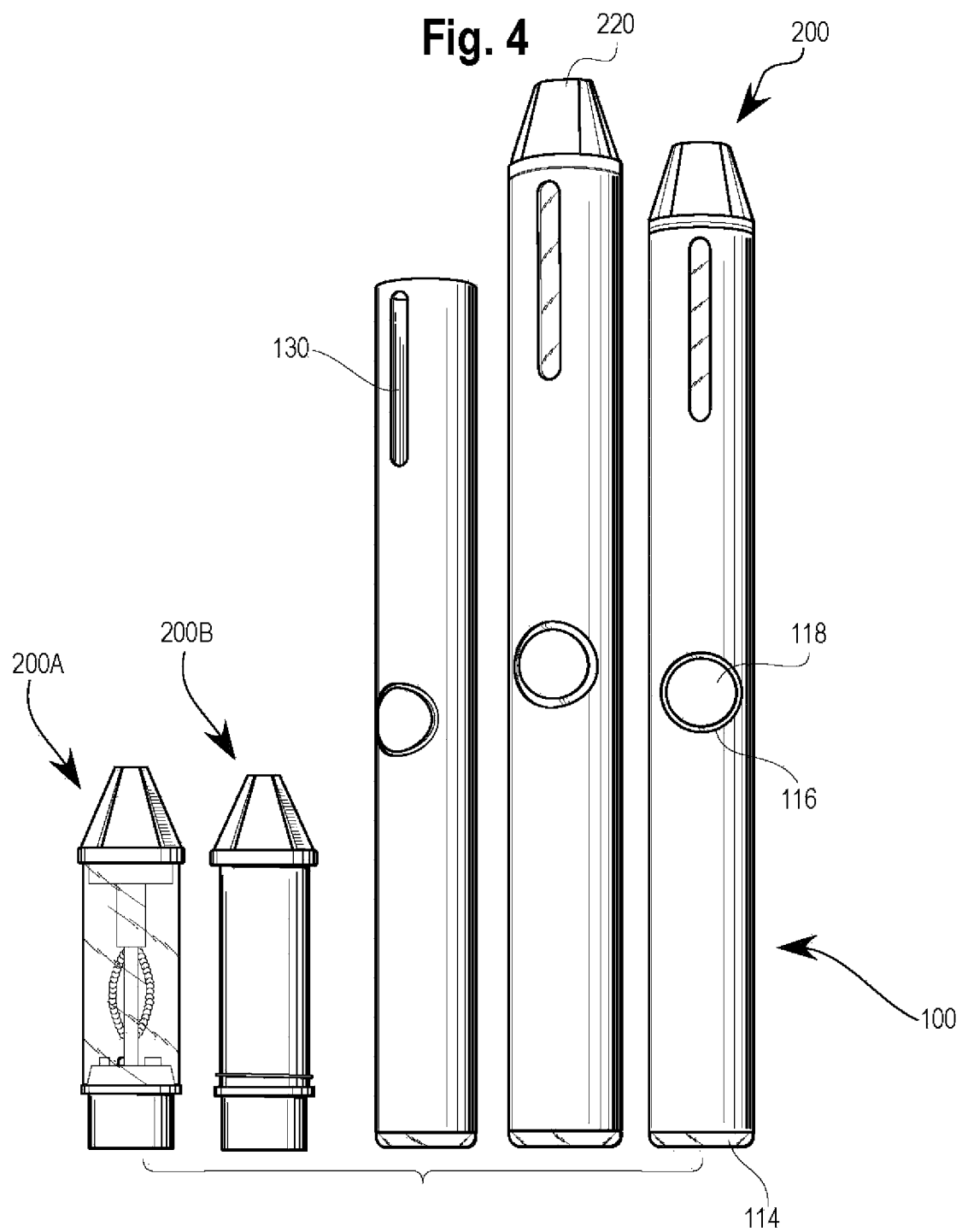
FIGS. 4-7 illustrate embodiments of electronic cigarettes comprising the first battery portion of FIGS. 1-3 and the cartomizers of FIGS. 1 and 2, in accordance with the disclosure.
Figure 5:
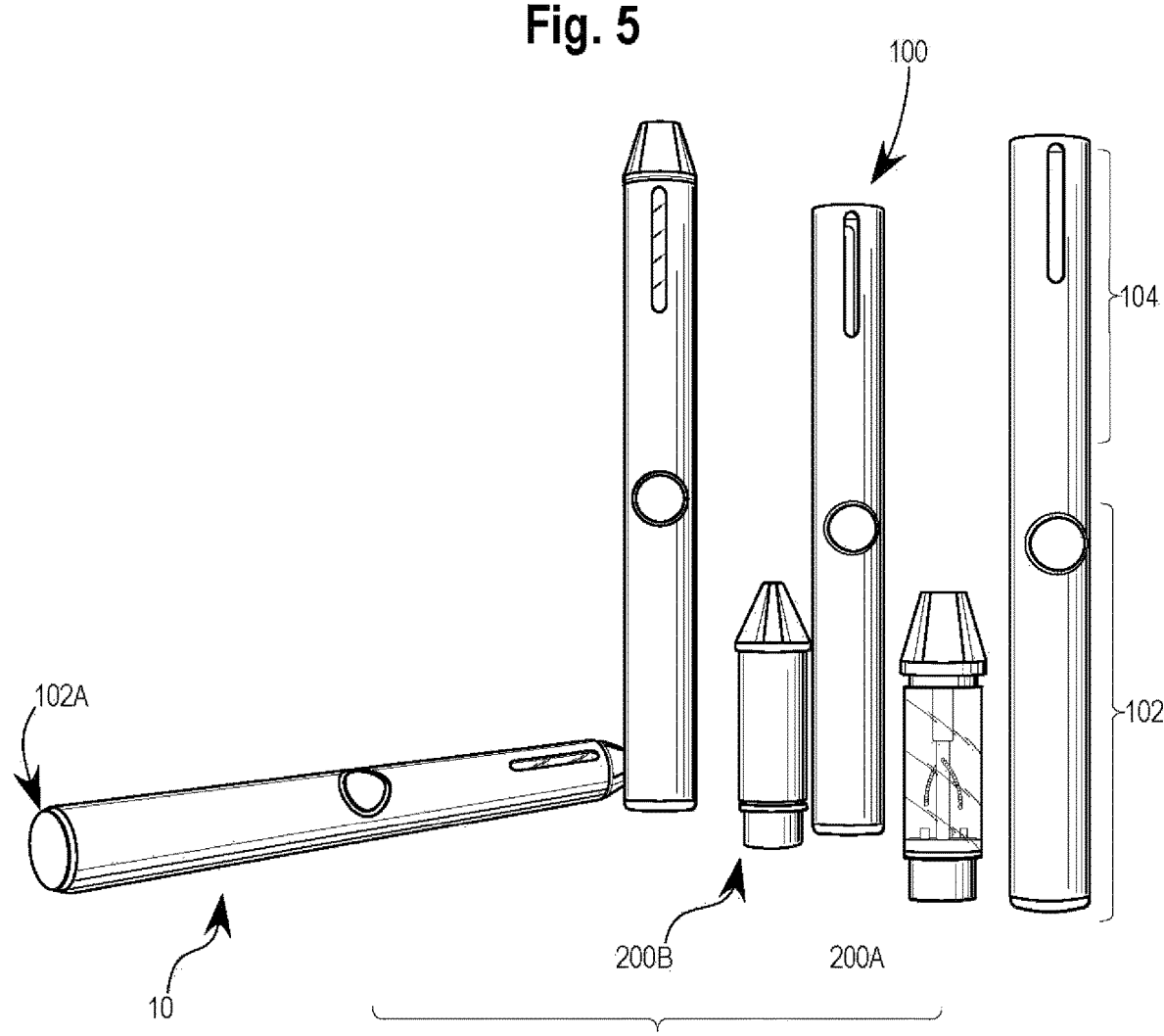
Figure 6:
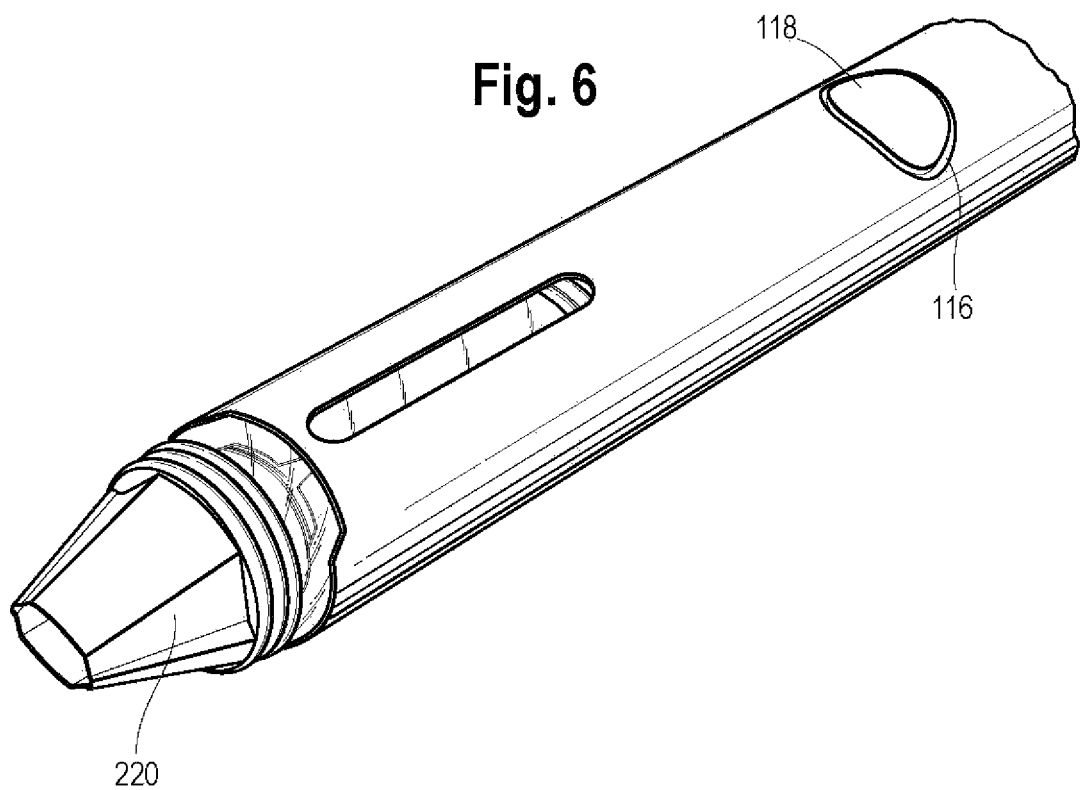
Figure 7:
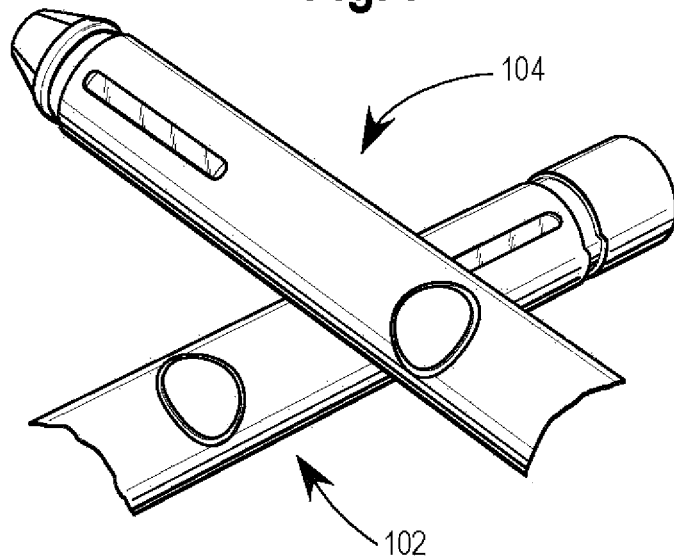

As shown in FIG. 3, a charger 400 may be inserted into chamber 108 (FIG. 1) in order to charge battery 110 (FIG. 1) in embodiments where battery 110 may be rechargeable. Through its insertion into chamber 108 and contact with connector 120, charger 400 may provide an electrical charge to battery 110. Charger 400 may include a plug 410 for connecting charger 400 to a power source, which in one embodiment is a wall socket. Other plugs 410 for different power sources are contemplated within the disclosure, including USB connections and other known or to be developed power sources. An indicator light 420, which may be an LED light, may be provided on charger 400 in order to indicate a charging status, for instance when charger 400 is connected with a power source. PCB 112 may operate to change other indicators, for instance LED indicators 114/116, to indicate the charging status of electronic cigarette 10. In accordance with the disclosure, and illustrated for instance in FIG. 9, charger 400 may be connectable to battery portion at or proximate to first end 102A. Furthermore, as also illustrated for instance in FIG. 9, charger magnets 404 are contemplated within the disclosure in order to securely couple charger 400 to battery portion 100. In one embodiment, a metallic surface 404 is provided and positioned so as to be adjacent to magnets 124 or magnets 162 (depending on the embodiment of the disclosure). In another embodiment, a metallic surface 124 or 162 in order to magnetically couple battery portion 100 with charger magnets 404. Additionally, charger magnets 404 may be provided having opposing polarities as battery portion magnets 124 or 162.

FIGS. 4-7 further illustrate the embodiments of electronic cigarette 10 provided in FIGS. 1-3, in accordance with the disclosure.

Figure 8:
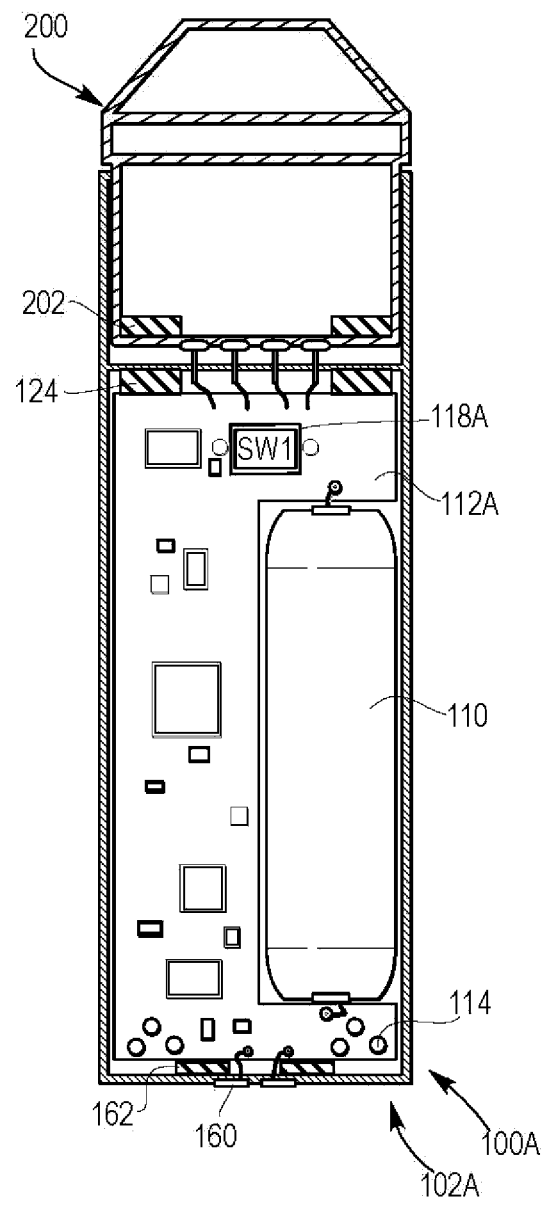
FIG. 8 illustrates a front view of an embodiment of an electronic cigarette, in accordance with the disclosure, comprising a second embodiment of a battery portion with the outer shell of the second embodiment battery portion shown transparently so as to illustrate the inner components of the electronic cigarette.
Figure 9:
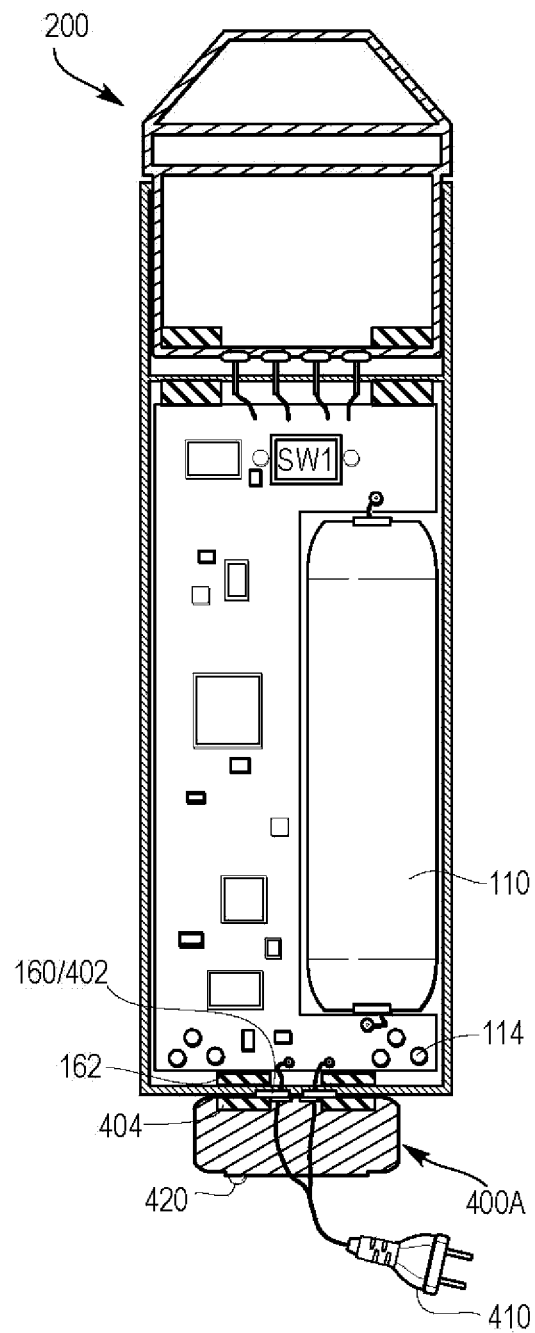
FIG. 9 illustrates a front view of the electronic cigarette of FIG. 8 with a charger attached, with the outer shell of the second embodiment battery portion shown transparently so as to illustrate the inner components of the electronic cigarette.

FIGS. 8 and 9 illustrate an additional embodiment of an electronic cigarette 10 having a battery portion 100A for receiving a cartomizer such as cartomizer 200 or cartomizer 200B. PCB 112 may operate to perform a variety of functions including, such vaporization temperature control or regulation, voltage boost, accelerometer, or various drivers for controlling LED functioning. One or more LED indicators 114 may be provided and, in one embodiment, a set of three LED lights of variable colors are provided proximate to battery end 102A of the battery portion 100A. Magnets 124/202 may be provided in order to retain cartomizer 200 within cartomizer chamber 108. A switch 118A may be provided in order to manually activate or otherwise control electronic cigarette 10.

A battery charger 400A, having charging contacts 402, may be attached or connected to charging contacts 160 provided on outer shell 106, or otherwise exposable to the environment. In one embodiment, charging contacts 160 are positioned at or proximate to battery end 102A. Charging contacts 160, 402 may include a first positive contact and a second negative contact. In order to secure charging contacts 160 against corresponding charging contacts 402 of charger 400A, one or more magnets 162 may be provided proximate to charging contacts 160. Magnets 162 may then be capable of engaging with charger magnets 404 provided on portion of charger 400A such that magnets 162, 404 are adjacent to each other when contacts 160, 402 are contacting one another. In order to ensure the proper alignment of contacts 160, 402, two magnets 162 may be provided with opposed polarities, and two charger magnets 404 may be provided with opposed polarities. These opposed polarities may ensure proper orientation of charger 400A when it is connected to battery portion 100A. In some embodiments, battery portion magnet(s) 162 may operate to magnetically attract and connect a metallic charger surface 404, or charger magnets 404 may operate to magnetically attract and connect a metallic battery surface 162, each of these embodiments thereby operating to magnetically couple charger 400 with battery portion 100. An indicator light 420, which may be an LED, may be provided to indicate a charging status of battery 110. A charging extension 410 may be provided so as to connect charger 400A to a power source or, alternatively, a power source may be internally provided within charger 400A. Charging extension 410 may be an AC wall adapter to USB and USB cord to magnetic plug. Any charger 400 of the disclosure may contain OverVoltage and OverCurrent protection in order to prevent over charging of battery 110 thereby assuring long battery life and in order to reduce the likelihood of battery 110 overheating. In one embodiment, charger 400 is rated at approximately 1000 mA current, which for some embodiments will equate to approximately two hours of battery life. The battery life will vary depending on battery selection and number of batteries 110 used in a given embodiment.

Figure 10:
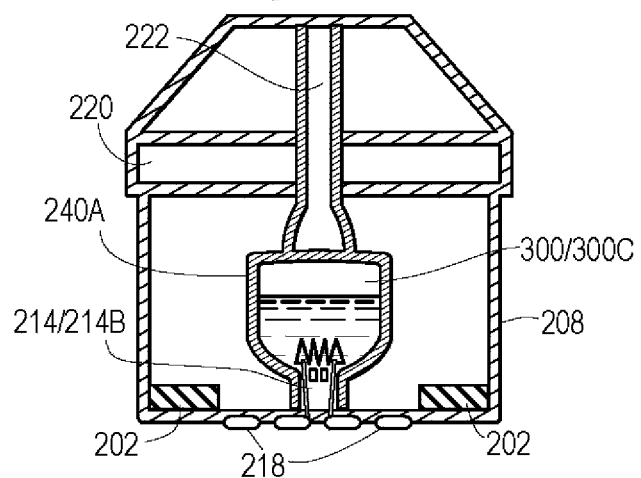
FIG. 10 illustrates a front cross sectional view of an embodiment of a cartomizer in accordance with the disclosure.

Referring now to FIG. 10, an embodiment for a cartomizer 200C is provided for holding a vaporizable substance 300. Cartomizer 200C may be used as an alternative cartomizer to 200/200B cartomizers, for example. Vaporizable substance 300 in cartomizer 200C may be a wax, oil or gel 300C. In cartomizer 200C, heating element 214 may be provided at the base of a basin 214B, which may or may not be removable from cartomizer body 208. Basin 214B may be dimensioned to hold wax, oil or gel 300C while heating element 214 may elevate the temperature within basin 214B to a vaporization temperature range, as controlled by PCB 112. Once the wax, oil or gel 300C is vaporized, a user may inhale the vapor through an inhalation tube 222 and out through mouthpiece 220. In some embodiments, mouthpiece 220 is removable through a friction fit, threaded connection, or any other known or to be developed connection means. One or more O-ring seals may also be provided proximate to the mouthpiece to ensure a fluid tight connection between mouthpiece 220 and cartomizer body 208.

Figure 11:
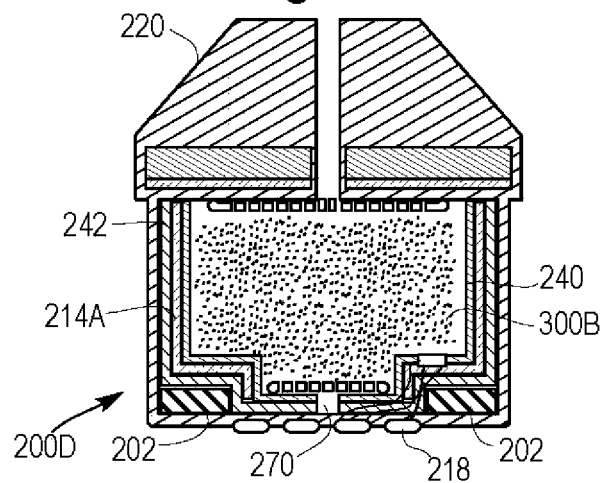
FIG. 11 illustrates a front view of an embodiment of a cartomizer in accordance with the disclosure.

FIG. 11 shows an additional embodiment of a cartomizer 200D for holding a dry vaporizable substance 300B. Cartomizer 200D may be used as an alternative cartomizer to 200/200B cartomizers, for example. Dry substance 300B may be held in a removable liner or container 240. Cartomizer 200D may also include heating element 214A and insulation material 242, each of which may be similarly provided and oriented as previously described with respect to cartomizer 200B. An air flow hole or aperture 270 may be provided at the base of cartomizer 200D. This airflow hole 270 may be provided off plane or misaligned with respect to electrical contacts 218. Airflow hole 270 may align with a hole between chamber 108 and battery portion 100A, which may house a fan 190 as described below. A temperature sensor 260 may also be included.

FIG. 12 further illustrates the embodiments of an electronic cigarette 10 provided in FIGS. 9-11 in accordance with the disclosure.

Figure 15:
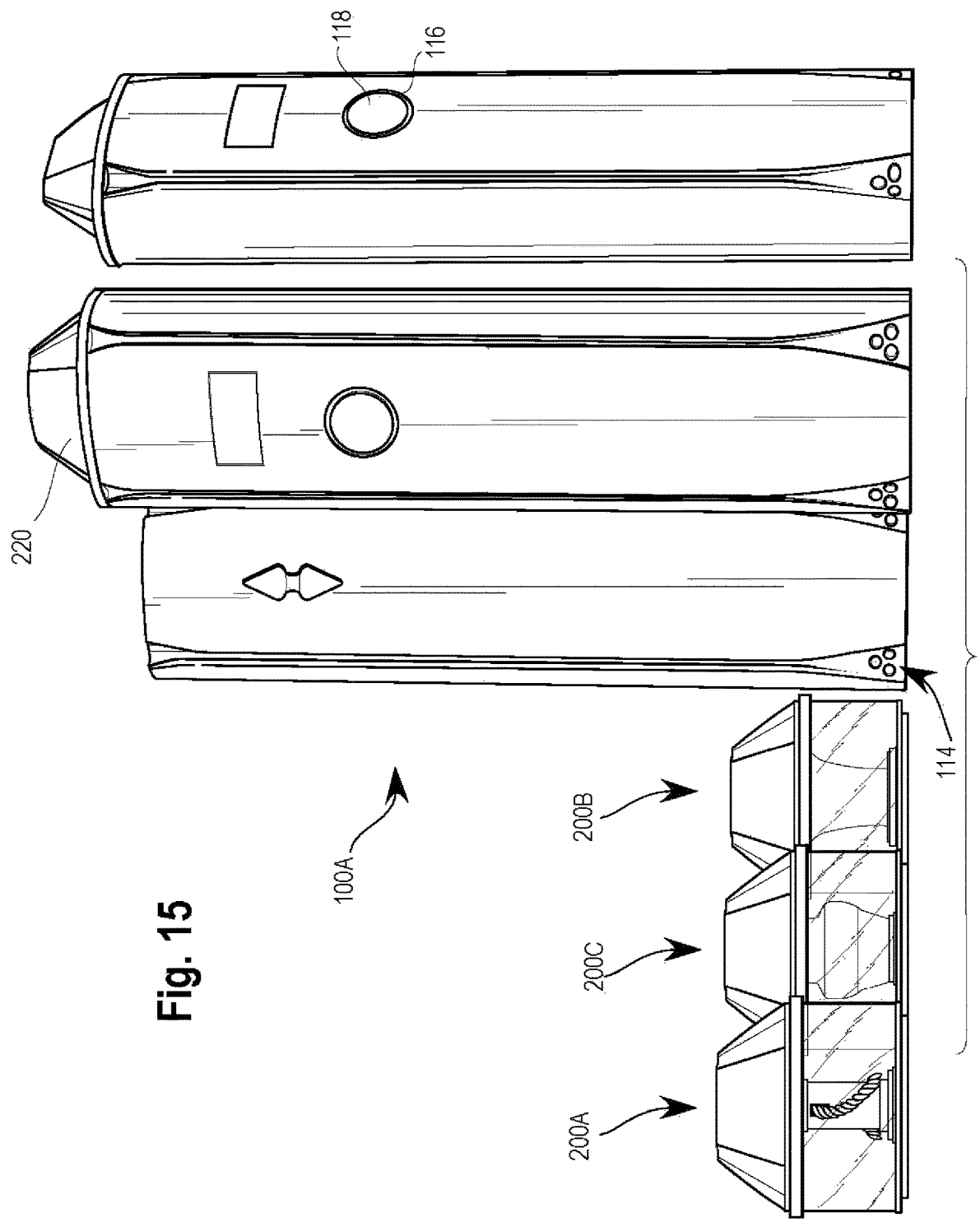
FIG. 15 illustrates embodiments of the electronic cigarette of FIGS. 13-14 in accordance with the disclosure.

Referring now to FIG. 13, an embodiment of an electronic cigarette 10 including a battery portion 100B is provided. PCB 112 may include a microcontroller, voltage boost integrated circuit, accelerometer, and a Fan control circuitry. A fan 190, including blades and a motor, may be provided internally in battery segment 110 of battery portion 100B. Fan 190 may operate to facilitate air flow from external battery portion 100B, such as through one or more holes 152 provided in outer shell 106, through battery segment 110 and into cartomizer thereby establishing an air flow for inhalation in accordance with the disclosure. In some embodiments, fan 190 has a reversible operation in order to "clear" the air flow path in the event debris or excess vapor is caught in the air flow path. PCB 112 may also include one or more switches that, for instance, may be provided beneath control buttons, such as that exemplified in FIG. 15). PCB 112 may also include one or more LED's for these and other similar switch lights. PCB 112 may also operate to display a status message on an LED screen, which may be provided on outer shell 106 (e.g., as shown in FIG. 15). A status message may, for example, include messages to indicate a status of the electronic cigarette 10, such as when the cigarette 10 is activated, charging, or has reached a vaporization temperature. An LED screen may also display warning or error messages, for instance a danger message when a critical temperature has been detected by a sensor. Further, as illustrated in FIG. 14. In some embodiments, PCB 112 may operate to recognize the cartomizer 200/200A/200B/200C inserted into chamber 108, and in order to identify the vaporizable substance 300 included in cartomizer 200. For instance, PCB 112 may communicate with sensor 260 in cartomizer 200 in order to identify both the type and amount of vaporizable substance 300 within cartomizer 200. This identification may be included in the status message displayable on the LED screen on outer shell 106. Charger 400A may be utilized for charging battery 110 in battery portion 100C. It should be understood and appreciated that, in some embodiments, charger 400A may be inserted into chamber 108 of battery portions 100A/100B in addition to connection of charger 400A as described herein. It should be further understood and appreciated that in embodiments where charger 400/400A is coupled with battery portion 100 at a position other than where cartomizer 200 is connected, such as embodiments where charger 400A is coupled at or proximate to first end 102A, electronic cigarette 10 may operate with a pass through function, namely the ability to operate electronic cigarette 10 while the unit is charging from charger 400A.

FIG. 15 further illustrates the embodiments of an electronic cigarette 10 provided in FIGS. 13-14 in accordance with the disclosure.

Certain charger embodiments for rechargeable vaporizers or electronic cigarettes disclosed hereinabove, for example in FIG. 3, employ electrical contacts between the charger and the cartomizer portion's electrical connector. Under these circumstances, the cartomizer portion is first removed from the chamber to expose the electrical connector and thereafter a charger with compatible electrical contacts is inserted into the chamber. The invention contemplates other types and locations of connectors on the vaporizer and charger. Accordingly, in certain embodiments, the present invention provides a charger 400 for charging a vaporizer or electronic cigarette having charging contacts attached essentially transversely to its outer shell at an end distal to the cartomizer receiving portion and proximate to its battery portion. One such embodiment is shown in FIG. 14. In some of these embodiments where the cartomizer portion is not removed from the vaporizer to expose the electrical connector, the charging contacts are incorporated into the device such that the vaporizer or electronic cigarette may be operated in its typical fashion during the recharging of the battery ("pass-through" charging).

Figure 16:
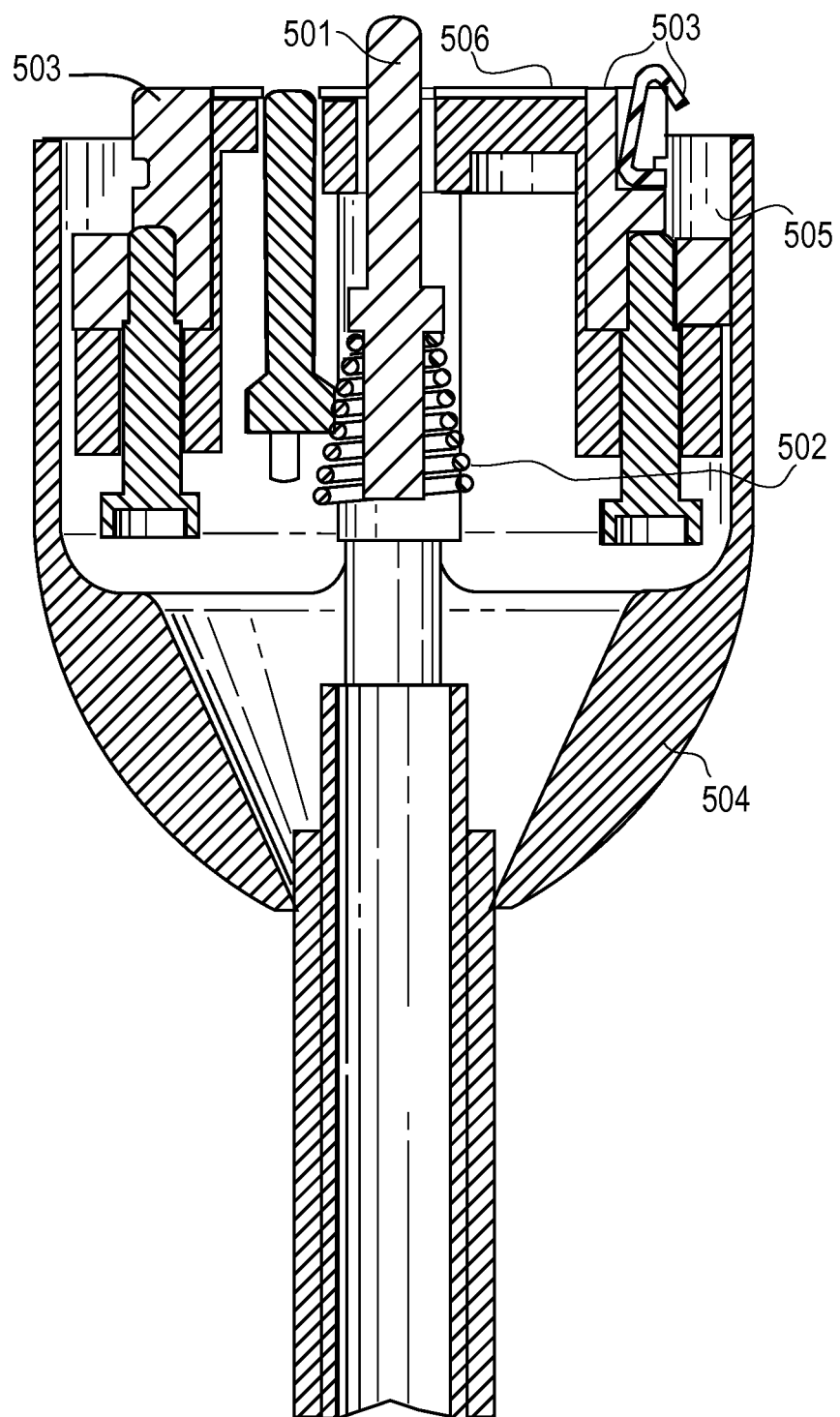
FIG. 16 illustrates a longitudinal cross sectional view of an embodiment of charger contacts on a power cord of a vaporizer or electronic cigarette charger of the present invention.
Figure 17:
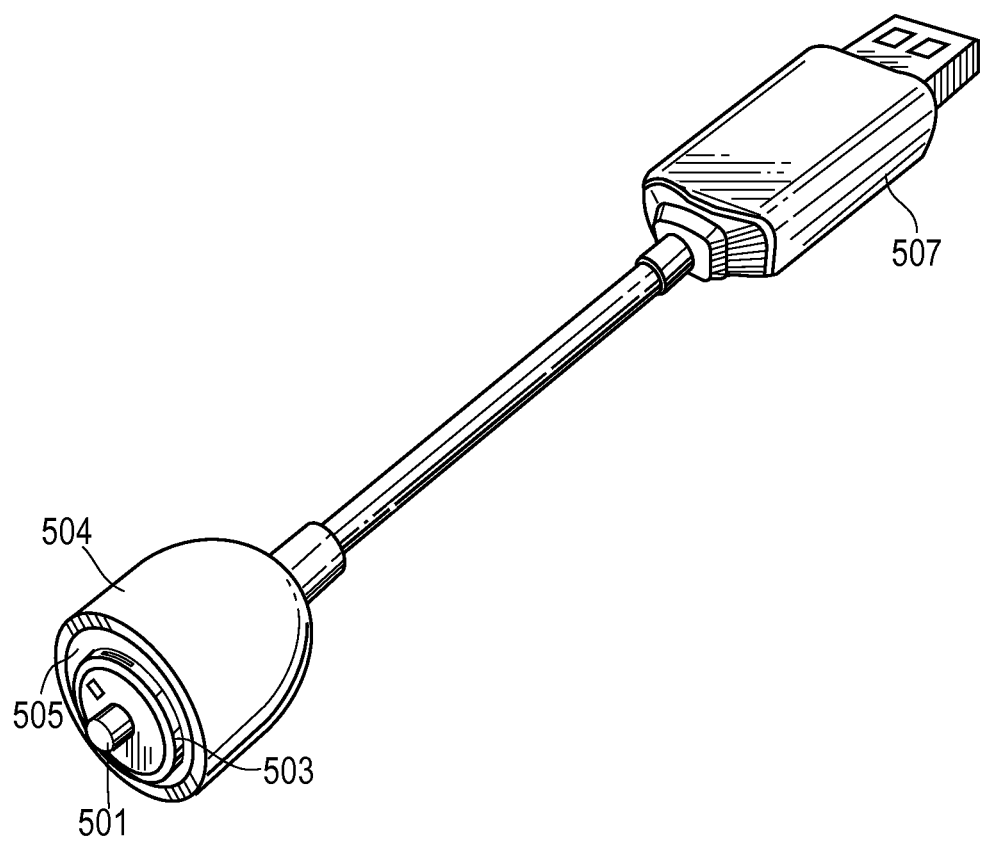
FIG. 17 illustrates a perspective view of an embodiment of charger contacts on a power cord of a vaporizer or electronic cigarette charger of the present invention.

Still other embodiments for chargers and rechargeable vaporizers or electronic cigarettes are illustrated in FIGS. 16, 17, 18, 19, and 20. For example, FIG. 16 depicts aspects of the portion of the charger that connects with the vaporizer during the charging operation. In this example, the positive connection to the vaporizer's charging contacts is facilitated through the use of a spring-loaded pogo pin (see 501 and 502). The negative connection pin (503) or other negative connection is isolated from the pogo pin by an insulator 506 to isolate the positive and negative connections from each other. At the contacts insulator surface such that it is isolated from electrical connections 501 and 503 is a wiper contact that is capable of powering a LED charging indicator light. In some instances the exterior housing 504 for the charger is at least in part, translucent or transparent, so that the indicator lamp can be readily observed. To maintain readily removable connectivity with the vaporizer, a magnet 505 is provided, and is typically in proximity to the outer edges of the charger's charging contacts and optionally takes the form of a ring disposed in substantially concentric fashion about the assembly containing the electrical contacts and insulation. The charger is generally held in the correct position for charging by magnetic attraction to the vaporizer's charging contacts. The magnetic attraction strength is such that the charger can be easily detached by just pulling on the charger. This level of attractive force may also allow the charger to break away if it is pulled too far away from the battery portion of the vaporizer so that no significant damage will occur to the vaporizer or the charger. Other aspects of the charger include one or more of support pieces and/or fixing screws, for example. The materials employed in the construction of the charger would be readily understood by the ordinarily skilled artisan once equipped with the teachings of the present invention. Any material that conducts electricity will generally be acceptable where transfer of electricity to charge the battery is required. Similarly, where insulation is a necessary property for normal operation, electrically non-conductive materials are typically acceptable. FIG. 17 illustrating a perspective drawing of a charger that employs a USB terminus connection 507 as a source of power for the charging operation. At the end distal to the USB terminus are the charger's charging contacts for the vaporizer or electronic cigarette, including a pogo pin-type positive connection 501, an insulator 506, a negative connection 503, a magnet 505 and a housing 504.

Figure 18:
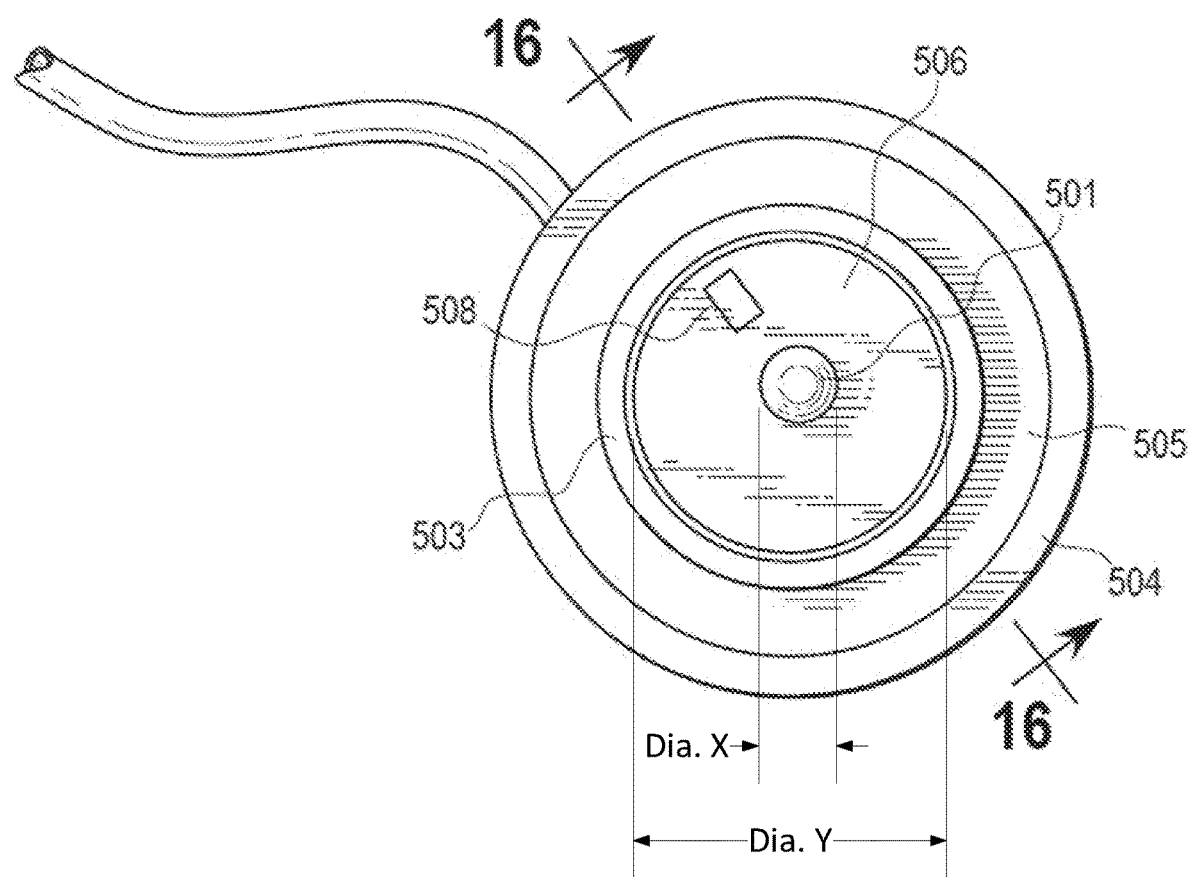
FIG. 18 illustrates a lateral view of an embodiment of charger contacts on a power cord of a vaporizer or electronic cigarette charger of the present invention.

FIG. 18 shows an alternate end on view of a charger's electrical contacts region, depicting a housing 504, magnet 505, negative connection 503, wiper contact 508 for an optional LED-type charging indicator light disposed on the housing, pogo pin-type positive connection 501, and insulator 506.

Figure 19:
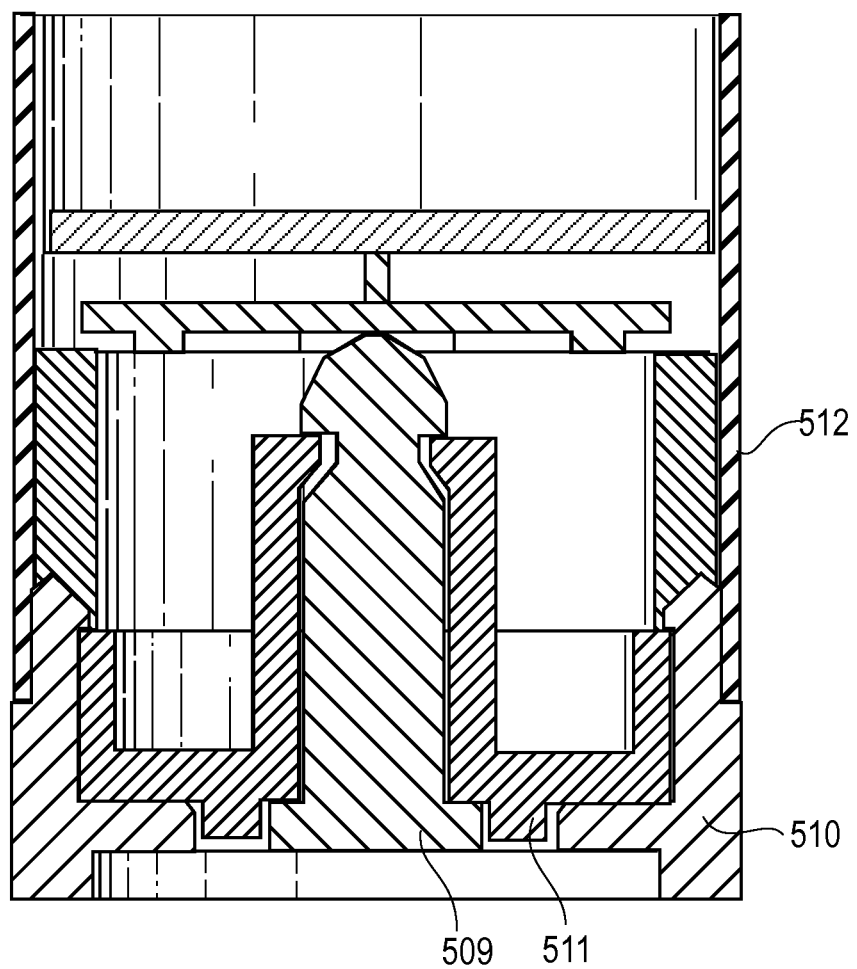
FIG. 19 illustrates a longitudinal cross sectional view of an embodiment of charger contacts of a vaporizer or electronic cigarette for connecting with a vaporizer or electronic cigarette charger of the present invention.

FIG. 19 illustrates a partial longitudinal cross section view of an embodiment of the vaporizer's electrical connector attached essentially transversely to its outer shell 512 at an end distal to the cartomizer receiving portion and proximate to its battery portion, which may be contacted with the chargers contacts illustrated in FIG. 18. FIG. 19 shows an arrangement of components for an embodiment of present invention's electrical connector including a positive contact 509, negative contact 510, and insulation 511.

Figure 20:
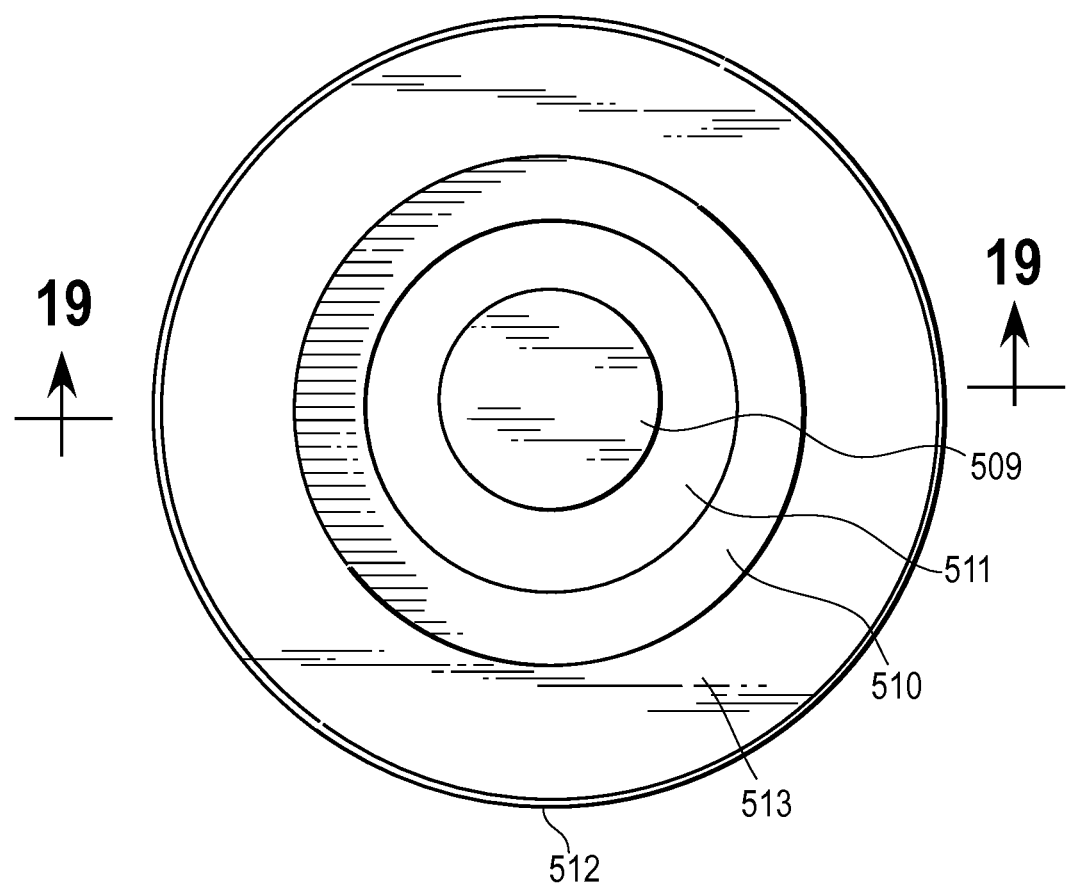
FIG. 20 illustrates a lateral cross sectional view of an embodiment of charger contacts on a vaporizer or electronic cigarette for connecting with a vaporizer or electronic cigarette charger of the present invention.

An alternative vaporizer electrical connector compatible with the charger shown in FIG. 18 is shown in FIG. 20 in an end on view. In this view, the positive contact 509 forms an innermost circle, surrounded by concentric circles of independently varying dimensions including an insulator 511, a negative contact 510, a magnet 513 and outer shell 512. In certain embodiments 513 may be a magnet or a magnetic material. In embodiments where 513 is a magnetic material, it is preferably magnetic metal, more preferably a ferromagnetic metal. The magnetic attraction between 513 and the magnet in the charger contacts is strong enough to hold the charger contacts and vaporizer charging contacts sufficiently so that the battery may be recharged. In certain preferred embodiments, the attraction is sufficiently strong to maintain the charger/vaporizer connection, but weak enough to be disconnected without substantial damage to the charger or the vaporizer.

Figure 21:
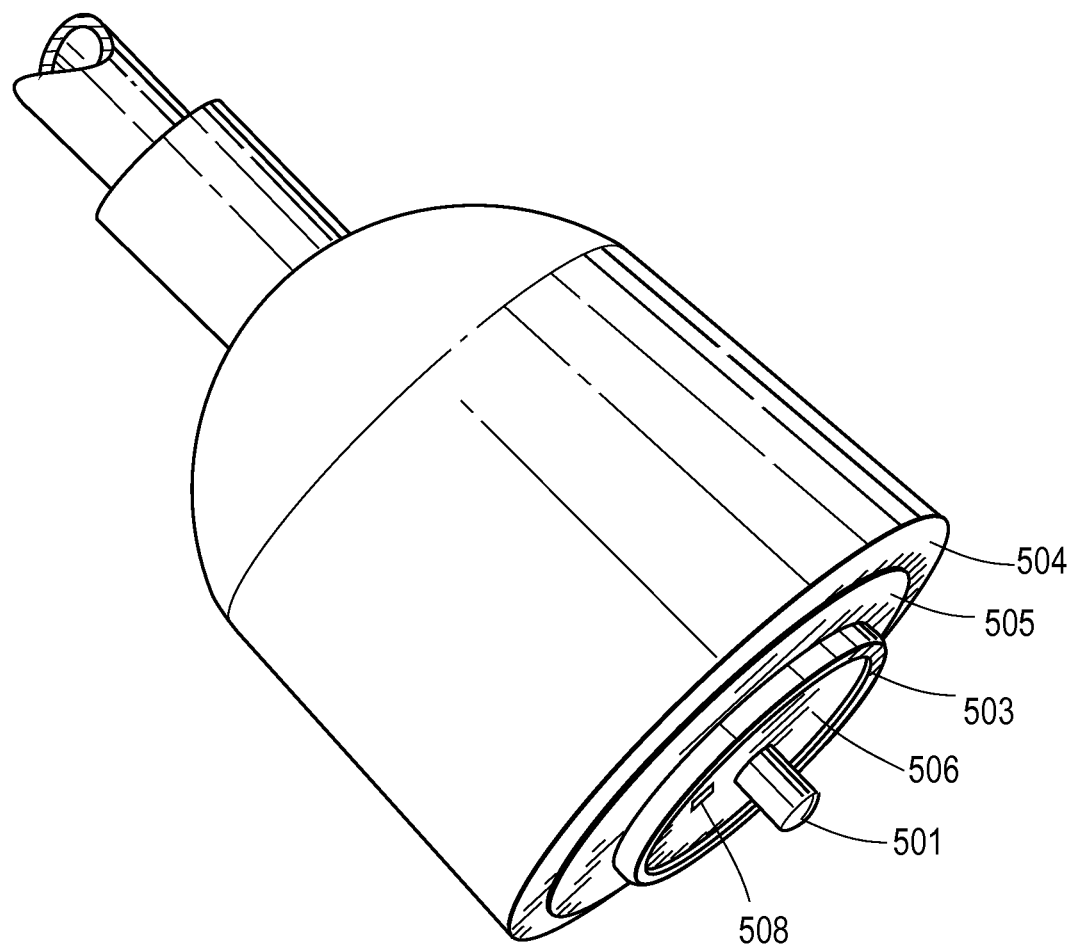
FIG. 21 illustrates a perspective view of an embodiment of charger contacts on a power cord of a vaporizer or electronic cigarette charger of the present invention.

FIG. 21 shows a perspective side on view of the FIG. 18 charger's electrical contacts region depicting a housing (504), magnet (505), negative connection (503), wiper contact (508), pogo pin-type positive connection (501), and insulator (506).

Figure 22:
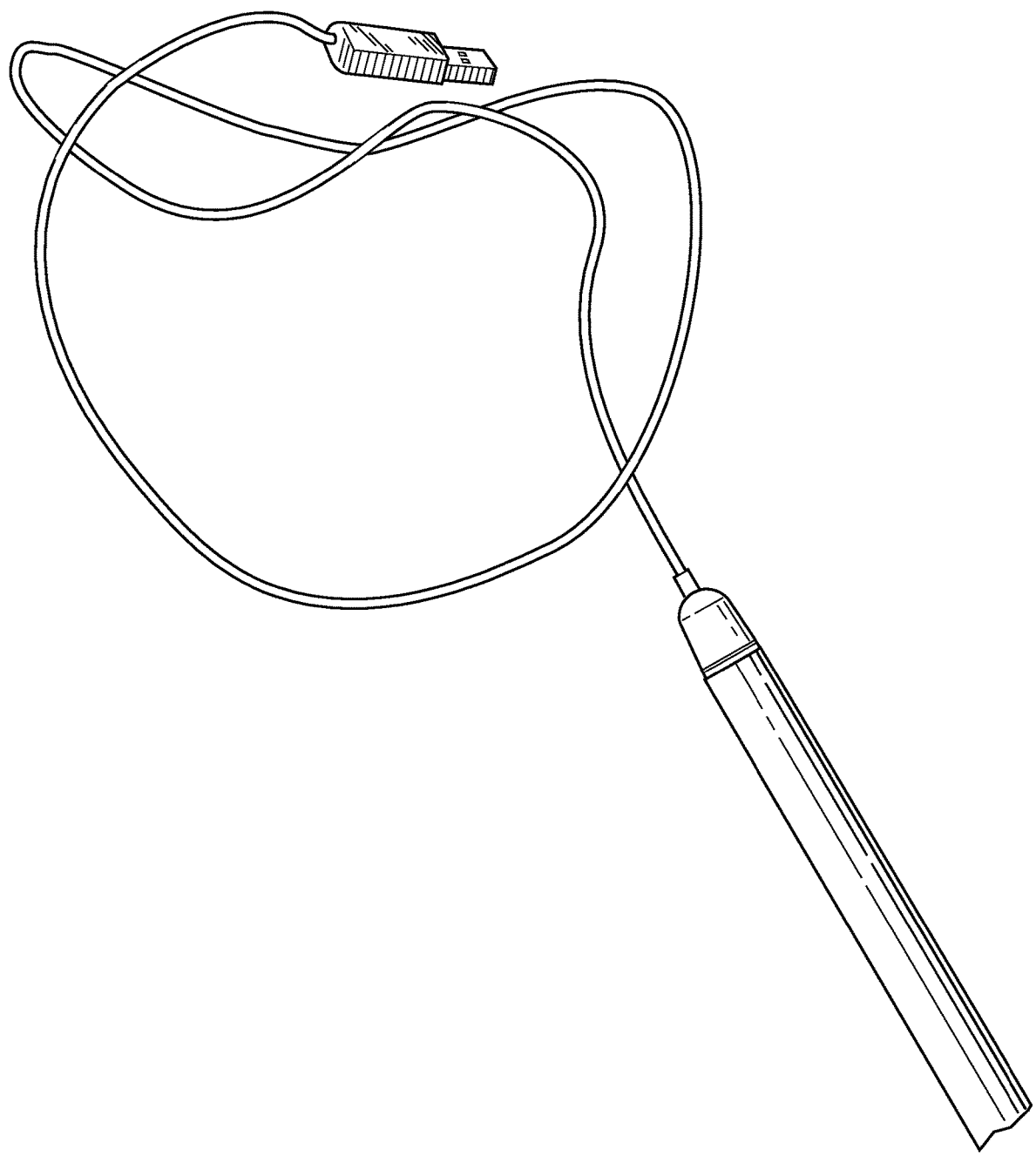
FIG. 22 illustrates a side view of an embodiment of a charger of the present invention in contact with charger contacts of a vaporizer or electronic cigarette for charging a vaporizer or electronic cigarette battery.

FIG. 22 shows the charger of FIG. 18 connected for recharging to the electrical connector of the vaporizer compatible with the charger shown in FIG. 20.

Vaporizer or electronic cigarette charger kits useful in, for example, the recharging of batteries used to power the vaporization process in such devices, are also within the ambit of the present invention. These kits typically include one or more chargers of the present invention, or alternatively a charger with multiple interchangeable power connectors (e.g., wall plug and USB connector). Such kits may further include, if desired, one or more of various compatible vaporizers or electronic cigarettes, their components, such as for example, one or more interchangeable cartomizers, cartomizer refills, etc., as will be readily apparent to those skilled in the art. Instructions, either as inserts or as labels, indicating quantities of the components contained in the kit, guidelines for operation or use, and/or guidelines for connecting any of the components and/or refilling the cartomizers, may also be included in the kit.

In accordance with certain embodiments of the present invention, there are provided methods which comprise contacting a charger of the present invention with a compatible vaporizer or electronic cigarette for a time and under conditions effective to recharge a rechargeable battery contained within said vaporizer or electronic cigarette sufficient to repower vaporizer or electronic cigarette for its continued use.

As will be understood by the ordinarily skilled artisan equipped with the disclosure herein, electrical contacts compatible with the charger must be provided for on or within the vaporizer or electronic cigarette.

The descriptions set forth above are meant to be illustrative and not limiting, and persons of skill in the art will recognize that various common and known deviations from the above described structures are considered to be within the scope of the disclosed concepts described herein.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

LIST OF REFERENCES

10 Electronic Cigarette
100 Battery Portion
100A Battery Portion
100B Battery Portion
102 Battery Housing Segment
102A First end of Battery Portion
104 Cartomizer Receiving Segment
104A Second end of Battery Portion
106 Shell
108 Cartomizer Chamber
110 Battery
112 PCB
112A PCB
114 Indicator
116 Ring Indicator
118 Button
118A Switch
120 Electrical Connector
122 Pin
124 Magnet
126 Protrusion
130 Window
152 Hole
160 Charging Contact
162 Magnet
190 Fan
200 Cartomizer
200A Cartomizer
200B Cartomizer
200C Cartomizer
202 Magnet
204 Groove
208 Body
210 Insertion End
212 Mouthpiece End
214 Heating Element
214A Heating Element
214B Basin
216 Wick
218 Electrical Contact
220 Mouthpiece
222 Inhalation Tube
224 Threading
226 Bushing
228 Colored Ring
240 Container
242 Insulating Material
250 Screen
252 Hole
260 Sensor
300 Vaporizable Substance
300A Vaporizable Fluid
300B Vaporizable Dry Substance
300C Vaporizable Wax
400 Charger
400A Charger
402 Electrical Contact
404 Magnet
410 Plug
420 Light
501 pogo pin
502 spring
503 negative connection pin
504 exterior housing
505 magnet
506 insulator
507 USB terminus connection
508 wiper contact
509 positive contact
510 negative contact
511 insulation
512 outer shell
513 magnet or magnetic metal

What is claimed:

1. A vaporizer comprising:
a shell comprising a battery portion and a cartomizer receiving portion, said battery portion comprising a rechargeable battery and electronic control circuitry; and
charging contacts, wherein the charging contacts are attached to said shell and extend essentially transversely from an end of said shell, said end of said shell located distal to the cartomizer receiving portion and proximate to said battery portion; and
a longitudinal axis extending from the cartomizer receiving portion to the charging contacts;
wherein the charging contacts include (a) a positive electrical contact and a negative electrical contact insulated from each other, and (b) a first magnet, the positive electrical contact, the negative electrical contact, and the first magnet configured for contacting a compatible charger in order to charge the rechargeable battery;
wherein the first magnet concentrically surrounds the positive electrical contact and the negative electrical contact;
wherein one of the electrical contacts includes a first surface and a second surface and the other of the electrical contacts includes a third surface, the second surface and the third surface each being recessed from the first surface along the longitudinal axis, and the first surface, the second surface, and the third surface are each flat and each extends perpendicularly to the longitudinal axis.

2. A kit comprising:
a vaporizer charger comprising:
a housing comprising an exterior end surface;
a power source portion;
charging contacts; and
a longitudinal axis extending from the housing to the charging contacts:
wherein said charging contacts are attached to the housing, said charging contacts including (a) a positive electrical contact and a negative electrical contact insulated from each other, and (b) a first magnet, the positive electrical contact, the negative electrical contact, and the first magnet each proximately disposed at the exterior end surface and configured for charging a rechargeable battery of a vaporizer compatible with said charger;
wherein the first magnet includes a first surface and concentrically surrounds the positive electrical contact and the negative electrical contact; and
wherein one of the electrical contacts includes a second surface and the other of the electrical contacts includes a third surface, the second surface and the third surface each protruding from the first surface along the longitudinal axis, wherein the second surface protrudes farther from the first surface along the longitudinal axis than the third surface protrudes from the first surface along the longitudinal axis; and a vaporizer, said vaporizer comprising:
  a shell comprising a battery portion and a cartomizer receiving portion, said battery portion comprising a rechargeable battery and electronic control circuitry; and
  charging contacts, wherein the charging contacts are attached to said shell and extend essentially transversely from an end of said shell, said end of said shell located distal to the cartomizer receiving portion and proximate to said battery portion; and
  a longitudinal axis extending from the cartomizer receiving portion to the charging contacts;
  wherein the charging contacts include (a) a positive electrical contact and a negative electrical contact insulated from each other, and (b) a first magnet, the positive electrical contact, the negative electrical contact, and the first magnet configured for contacting said vaporizer charger in order to charge the rechargeable battery;
  wherein the first magnet concentrically surrounds the positive electrical contact and the negative electrical contact; and
  wherein one of the electrical contacts includes a first surface and a second surface and the other of the electrical contacts includes a third surface, the second surface and the third surface each being recessed from the first surface along the longitudinal axis, and the second surface protrudes farther from the first surface along the longitudinal axis than the third surface protrudes from the first surface along the longitudinal axis.

3. A method of charging a vaporizer, comprising: connecting a charger to a power supply and contacting a charging contact of the charger with a charging contact of a vaporizer of claim 1.

4. The vaporizer of claim 1, wherein the first surface, the second surface, and the third surface are configured to contact the compatible charger in order to charge the rechargeable battery.

5. The vaporizer of claim 1, wherein the second surface is at a same longitudinal location along the longitudinal axis as is the third surface.

6. The vaporizer of claim 1, wherein the negative contact includes the first surface and the second surface and the positive contact includes the third surface.

7. A vaporizer comprising:
  a shell comprising a battery portion and a cartomizer receiving portion, the battery portion comprising a rechargeable battery and electronic control circuitry, the cartomizer receiving portion comprising a chamber configured to have a cartomizer received therein, the chamber having a base end proximate to the battery portion, the base end of the chamber comprising cartomizer contacts configured to electrically connect to mating contacts on an insertable end of the cartomizer when the cartomizer is received in the chamber, wherein the cartomizer contacts are located solely at the base end of the chamber;
  charging contacts disposed opposite the cartomizer receiving portion along a longitudinal axis of the shell, wherein the charging contacts are attached essentially transversely to the longitudinal axis at an end of the shell located distal to the cartomizer receiving portion and proximate to the battery portion, wherein the charging contacts include a positive electrical contact and a negative electrical contact insulated from each other; and
  a first magnet disposed proximate to the charging contacts,
  wherein the positive electrical contact, the negative electrical contact, and the first magnet are configured to couple with a compatible charger in order to charge the rechargeable battery.

8. A system comprising:
the vaporizer of claim 7; and
a vaporizer charger comprising:
  a housing comprising an exterior end surface;
  a power source portion;
  a plurality of charging contacts proximately disposed at the exterior end surface and configured to charge the rechargeable battery; and
  a charger magnet disposed proximate to the charging contacts and configured to align the plurality of charging contacts of the vaporizer charger with the charging contacts of the vaporizer.

9. The vaporizer of claim 7, wherein the cartomizer includes a heating element and a basin configured to hold a vaporizable substance.

10. The vaporizer of claim 7, wherein the mating contacts of the cartomizer and the cartomizer contacts of the vaporizer are linearly arranged on a plane.

11. The vaporizer of claim 9, wherein the chamber includes an opening at a distal insertion end of the battery portion, and the chamber is configured to position the heating element of the cartomizer between the opening and the battery segment when the cartomizer is inserted into the chamber.

12. The vaporizer in accordance with claim 7, wherein the cartomizer contacts comprise pogo pins.

13. The vaporizer in accordance with claim 12, wherein the pogo pins extend into the chamber when the cartomizer is not received in the chamber, and wherein the pogo pins are contacted and at least partially compressed into the battery portion when the cartomizer is received in the chamber.

14. The vaporizer in accordance with claim 13, wherein the pogo pins are pressed against the mating contacts to establish an electrical connection between the battery portion and the cartomizer when the cartomizer is received in the chamber.

15. The vaporizer in accordance with claim 7, wherein a window is formed in the shell, the window provided on or proximate to the chamber to permit viewing of the cartomizer when the cartomizer is inserted in the chamber.

16. The vaporizer in accordance with claim 15, wherein the window is formed of a translucent material.

17. The vaporizer in accordance with claim 15, wherein the window comprises a slit cut into the shell.

18. The vaporizer in accordance with claim 9, wherein the cartomizer further comprises a cartomizer body, and wherein at least a portion of the cartomizer body is composed of a substantially translucent material to permit viewing of the vaporizable substance.

19. The vaporizer in accordance with claim 18, wherein a window is formed in the shell, the window provided on or proximate to the chamber to permit viewing of the cartomizer when the cartomizer is inserted in the chamber, and wherein the at least a portion of the cartomizer body composed of the substantially translucent material aligns with the window when the cartomizer is inserted into the chamber.

20. The vaporizer in accordance with claim 7, further comprising:
  a battery portion magnet disposed proximate to the chamber; and a cartomizer magnet disposed on a surface of the cartomizer, wherein the battery portion magnet and the cartomizer magnet are positioned so as to secure the cartomizer within the chamber when the cartomizer is inserted into the chamber.

21. The vaporizer in accordance with claim 7, wherein the charging contacts extend on an end of said shell perpendicularly to the longitudinal axis.

22. The vaporizer in accordance with claim 7, wherein the cartomizer contacts are configured to electrically connect at the base end of the chamber to the mating contacts on the insertable end of the cartomizer when the cartomizer is received in the chamber.

* * * * *

UNITED STATES PATENT AND TRADEMARK OFFICE
CERTIFICATE OF CORRECTION

PATENT NO. : 10,980,273 B2
APPLICATION NO. : 14/201267
DATED : April 20, 2021
INVENTOR(S) : Jan Andries Verleur et al.

It is certified that error appears in the above-identified patent and that said Letters Patent is hereby corrected as shown below:

On the Title Page

In the Foreign Patent Documents:
First Line, delete "201406215 A1 8/2014" and insert --2014206215 A1 8/2014--;

In the Related U.S. Application Data:
At Page 2, in item (60), first Line, delete "Provisional application No. 61/937,951" and insert --Provisional Application No. 61/937,851--.

Signed and Sealed this
Twenty-sixth Day of April, 2022

Katherine Kelly Vidal
*Director of the United States Patent and Trademark Office*